United States Patent [19]

Doscher

[11] Patent Number: 5,665,759
[45] Date of Patent: Sep. 9, 1997

[54] METHODS AND COMPOSITIONS FOR PROTECTING ANIMALS AGAINST ATTACK AND INFESTATION BY HELMINTH, ACARID AND ARTHROPOD ENDO- AND ECTOPARASITES

[75] Inventor: Mary Ehlers Doscher, Trenton, N.J.

[73] Assignee: American Cyanamid Company, Madison, N.J.

[21] Appl. No.: 306,072

[22] Filed: Sep. 14, 1994

Related U.S. Application Data

[60] Division of Ser. No. 842,283, Feb. 26, 1992, Pat. No. 5,371,239, which is a continuation-in-part of Ser. No. 455,685, Dec. 22, 1989, abandoned.

[51] Int. Cl.⁶ .................................................. A01N 43/36
[52] U.S. Cl. ............................................................ 514/427
[58] Field of Search ................................................ 514/427

[56] References Cited

U.S. PATENT DOCUMENTS

| | | | |
|---|---|---|---|
| 3,985,539 | 10/1976 | Bailey | 71/66 |
| 4,376,778 | 3/1983 | Ezaki et al. | 424/274 |
| 4,563,472 | 1/1986 | Inouye et al. | 514/381 |
| 5,008,403 | 4/1991 | Kameswaran | 548/561 |
| 5,162,308 | 11/1992 | Brown et al. | 514/63 |
| 5,204,332 | 4/1993 | Brown et al. | 514/63 |
| 5,232,940 | 8/1993 | Hatton et al. | 514/407 |
| 5,232,980 | 8/1993 | Kuhn et al. | 514/427 |
| 5,310,938 | 5/1994 | Brown et al. | 548/557 |

FOREIGN PATENT DOCUMENTS

A-0 372 263  6/1990  European Pat. Off.

OTHER PUBLICATIONS

Veterinary Pharmacology and Therapeutics, 6th Edition, 1988 pp. 849–860.
Veterinary Pharmacology and Therapeutics, 6th Edition, 1988 pp. 969–999.
Chemical Patents Index, Documentation Abstracts Journal, Section Ch, Week 9202, 11 Mar. 1992, ZA–A–9 010 354.
Chemical Patents Index, Documentation Abstracts Journal, Section Ch, Week 9139, 27 Mar. 1991, ZA–A–9 006 553.

*Primary Examiner*—Marianne M. Cintins
*Assistant Examiner*—Dwayne C. Jones
*Attorney, Agent, or Firm*—John W. Hogan, Jr.

[57] ABSTRACT

This invention relates to methods and compositions for treating, controlling, preventing and protecting warm-blooded animals from infestation and infection by helminths, acarids and arthropod endo- and ectoparasites by administering or applying to the animals a nitropyrrole or pyrrole carbonitrile compound.

16 Claims, No Drawings

METHODS AND COMPOSITIONS FOR PROTECTING ANIMALS AGAINST ATTACK AND INFESTATION BY HELMINTH, ACARID AND ARTHROPOD ENDO- AND ECTOPARASITES

This is a divisional of application Ser. No. 07/842,283 filed on Feb. 26, 1992 now U.S. Pat. No. 5,371,239 which is a continuation-in-part of Ser. No. 07/455,685 filed on Dec. 22, 1989 abandoned on Nov. 28, 1991.

BACKGROUND OF THE INVENTION

It is an object of this invention to provide a method for treating, controlling, preventing and protecting warm-blooded animals from infestation by helminths, acarids and arthropod endo- and ectoparasites, by administering thereto a nitropyrrole or pyrrole carbonitrile compound.

It is also an object of this invention to provide a prophylactic treatment for farm and companion animals including cattle, sheep, swine, horses, poultry, fish, rabbits, goats, dogs, cats and the like to prevent the development of helminthiasis in said animals.

These and other objects will become more apparent from the detailed description of the invention set forth below.

SUMMARY OF THE INVENTION

The present invention relates to methods and compositions for treating, controlling, preventing and protecting warm-blooded animals against infestation and infection by helminths, acarids and arthropod endo- and ectoparasites, by orally or parenterally administering or applying to said animals an anthelmintically, acaricidally or parasiticidally effective amount of a nitropyrrole or pyrrole carbonitrile compound.

DETAILED DESCRIPTION OF THE INVENTION

Nitropyrrole or pyrrole carbonitrile compounds useful in the present invention include those described in the following United States patent applications which are incorporated herein by reference: U.S. patent application Ser. No. 07/795,407, filed Nov. 20, 1991, which is a continuation-in-part of copending U.S. patent application Ser. No. 07/776,967, filed Oct. 15, 1991, which is a continuation of U.S. patent application Ser. No. 07/430,601, filed Nov. 6, 1989, now abandoned, which is a continuation-in-part of U.S. application Ser. No. 07/279,909, filed on Dec. 5, 1988, now abandoned.

A nitropyrrole or pyrrole carbonitrile compound suitable for the present invention has the following structure:

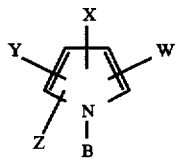

(I)

wherein

W is CN or $NO_2$;

X is CN, Br, Cl, I or $CF_3$;

Y is H, Br, Cl, I or $CF_3$;

Z is H, Br, Cl or I; and

B is

hydrogen,
- $C_1$–$C_6$ alkyl optionally substituted with one to three halogen atoms,
- one tri($C_1$–$C_4$ alkyl)silyl,
- one hydroxy,
- one cyano,
- one or two $C_1$–$C_4$ alkoxy groups optionally substituted with one to three halogen atoms,
- one $C_1$–$C_4$ alkylthio,
- one phenyl optionally substituted with one to three halogen atoms, one to three $C_1$–$C_4$ alkyl groups or one to three $C_1$–$C_4$ alkoxy groups,
- one phenoxy group optionally substituted with one to three halogen atoms, one to three $C_1$–$C_4$ alkyl groups or one to three $C_1$–$C_4$ alkoxy groups,
- one benzyloxy group optionally substituted on the phenyl ring with one to three halogen atoms, one to three $C_1$–$C_4$ alkyl groups or one to three $C_1$–$C_4$ alkoxy groups,
- one $C_1$–$C_6$ alkylcarbonyloxy group optionally substituted with one to three halogen atoms,
- one $C_2$–$C_6$ alkenylcarbonyloxy group optionally substituted with one to three halogen atoms,
- one phenylcarbonyloxy group optionally substituted with one to three halogen atoms, one to three $C_1$–$C_4$ alkyl groups or one to three $C_1$–$C_4$ alkoxy groups,
- one phenylcarbonyl group optionally substituted with one to three halogen atoms, one to three $C_1$–$C_4$ alkyl groups or one to three $C_1$–$C_4$ alkoxy groups,
- one $C_1$–$C_6$ alkoxycarbonyl group optionally substituted with one to three halogen atoms or one to three $C_1$–$C_4$ alkoxy groups,
- one benzyloxycarbonyl group optionally substituted on the phenyl ring with one to three halogen atoms, one to three $C_1$–$C_4$ alkyl groups or one to three $C_1$–$C_4$ alkoxy groups, or
- one $C_1$–$C_6$ alkyloxycarbonyloxy group optionally substituted with one to three halogen atoms,
- $C_3$–$C_6$ alkenyl optionally substituted with one to three halogen atoms or one phenyl group,
- $C_3$–$C_6$ alkynyl optionally substituted with one to three halogen atoms or one phenyl group,
- $C_1$–$C_6$ alkyl substituted with one to three halogen atoms and one $C_1$–$C_4$ alkoxy group, $C_3$–$C_6$ 1,2-alkadienyl, or cyano;

R is
- $C_1$–$C_6$ alkyl optionally substituted with one to three halogen atoms,
- one hydroxy,
- one cyano,
- one or two $C_1$–$C_4$ alkoxy groups optionally substituted with one to three halogen atoms,
- one $C_1$–$C_4$ alkylthio,
- one phenyl optionally substituted with one to three halogen atoms, one to three $C_1$–$C_4$ alkyl groups or one to three $C_1$–$C_4$ alkoxy groups,
- one phenoxy group optionally substituted with one to three halogen atoms, one to three $C_1$–$C_4$ alkyl groups or one to three $C_1$–$C_4$ alkoxy groups, one benzyloxy group optionally substituted on the phenyl ring with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one $C_2$–$C_6$ alkenylcarbonyloxy group optionally substituted with one to three halogen atoms, one phenylcarbonyloxy group optionally substituted with one to three halogen atoms, one to three $C_1$–$C_4$ alkyl groups or one to three $C_1$–$C_4$ alkoxy groups, one $C_1$–$C_6$ alkoxycarbonyl group optionally substituted with one to three halogen atoms or one to three $C_1$–$C_4$ alkoxy groups, or one benzyloxycarbonyl group optionally substituted on the phenyl ring with one to three halogen atoms, one to three $C_1$–$C_4$ alkyl groups or one to three $C_1$–$C_4$ alkoxy groups, $C_3$–$C_6$ alkenyl optionally substituted with one to three halogen atoms or one phenyl group, $C_3$–$C_6$ alkynyl optionally substituted with one to three halogen atoms or one phenyl group, phenyl optionally substituted with one to three halogen atoms, one or two $C_1$–$C_4$ alkyl groups, one or two $C_1$–$C_4$ alkoxy groups, $CF_3$, CN, $NO_2$, di($C_1$–$C_4$ alkyl)amino or $C_1$–$C_4$ alkanoylamino, phenoxy optionally substituted with one to three halogen atoms, one or two $C_1$–$C_4$ alkyl groups, one or two $C_1$–$C_4$ alkoxy groups, $CF_3$, CN or $NO_2$, di($C_1$–$C_4$ alkyl)amino or $C_1$–$C_4$ alkanoylamino, $C_1$–$C_6$ alkoxy optionally substituted with one to three halogen atoms, $C_2$–$C_6$ alkenyloxy optionally substituted with one to three halogen atoms, di($C_1$–$C_4$ alkyl)amino, N-($C_1$–$C_4$ alkyl)-N-phenylamino or N-($C_1$–$C_4$ alkyl)-N-halophenylamino, or $C_3$–$C_6$ polymethyleneimino.

The methods and compositions of the above invention are advantageous because they control and prevent helminth, acarid and arthropod endo- and ectoparasitic infestations and infections in warm-blooded animals, including cattle, sheep, swine, horses, poultry, fish, rabbits, goats, dogs, cats as well as humans.

Helminthiases is a widespread disease found in many farm and companion animals and is responsible for significant economic losses throughout the world. Among the helminths causing significant damage are the members of the class Trematoda, commonly known as flukes or flatworms, especially members of the genera Fasciola, Fascioloides, Paramphistomum, Dicrocoelium, Eurytrema, Ophisthorchis, Fasciolopsis, Echinostoma and Paragonimus. It has been found that the present invention is uniquely effective against trematodes and provides superior control of the economically important *Faciola hepatica*, commonly known as liver fluke.

For control of fluke infections and infestations the pyrrole carbonitrile compounds of formula I are preferred:

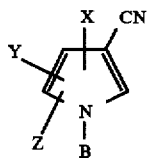

(I)

wherein

X is CN, Br, Cl, I or $CF_3$;

Y is H, Br, Cl, I or $CF_3$;

Z is H, Br, Cl or I; and

B is

hydrogen, $C_1$–$C_6$ alkyl optionally substituted with one to three halogen atoms, one or two $C_1$–$C_4$ alkoxy groups optionally substituted with one to three halogen atoms, one phenyl optionally substituted with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one phenylcarbonyl group optionally substituted with one to three halogen atoms, one to three $C_1$–$C_4$ alkyl groups or one to three $C_1$–$C_4$ alkoxy groups, or one $C_1$–$C_6$ alkoxycarbonyloxy group optionally substituted with one to three halogen atoms, or $C_1$–$C_6$ alkyl substituted with one to three halogen atoms and one $C_1$–$C_4$ alkoxy group;

R is phenyl optionally substituted with one to three halogen atoms, one or two $C_1$–$C_4$ alkyl groups, one or two $C_1$–$C_4$ alkoxy groups, $CF_3$, CN, $NO_2$, di($C_1$–$C_4$ alkyl)amino or $C_1$–$C_4$ alkanoylamino, $C_1$–$C_6$ alkoxy optionally substituted with one to three halogen atoms, or $C_2$–$C_6$ alkenyloxy optionally substituted with one to three halogen atoms.

It has further been found that flukicidal activity, including that exhibited by the above compounds, can be detected by an in vitro screening method utilizing free-living flatworms, preferably the fresh water planaria *Dugesia tigrina* and *Phagocata morgani*.

This screening method provides a unique and efficient in vitro means to detect the flukicidal activity of a broad spectrum of experimental compounds where costly and inefficient in vivo means have been required in the past.

In the screening method of the present invention, a non-lethal dosage of a compound to be tested for flukicidal activity is administered to a warm-blooded animal, preferably a gerbil, by feeding in the diet, orally by gavage, or parenterally. The non-lethal dosage for a given compound can be determined empirically or in accordance with the practices in the art for compounds of related type. The amount of the dosage also depends upon the method of administration.

After administration of the compound a period of time is allowed to pass for circulation of the compound to the animal's tissue. The amount of time depends on the method of administration of the compound, preferably after four days of feeding in the diet or two to twenty-four hours after oral gavage or parenteral administration. The animal is then sacrificed and tissue samples are dissected from the animal, preferably liver tissue. The type of tissue for subsequent steps of the screen is selected based upon factors including the type of free-living flatworms used in subsequent steps of the screen, the degree to which the test compound is circulated to a tissue type, and the target parasite. Where the selected tissue is liver, the dissected liver can be frozen and stored for later screening, or utilized immediately.

A portion of the dissected liver, either fresh or thawed if once frozen, is then administered to the flatworms. Administration of the liver to the flatworms is preferably accomplished by placing a portion of the liver in a liquid medium, preferably sterilized pond water, in which the flatworms are maintained, and observing for feeding. The liver is removed from the medium preferably within several hours from administration, more preferably after about two to four hours. Typically about 15 to about 50 mg of liver is applied to the medium per flatworm. After administration of the liver, the activity of the flatworms is observed and compared with that of flatworms fed on liver from untreated animal controls. Preferably each flatworm is kept separate from the other flatworms throughout the screen. Toxicity of the experimental compound is demonstrated by mortality or morbidity. Morbidity is demonstrated by unnatural activity including rapid movement, writhing or floating on the surface of the medium.

The ability of the screening method to detect flukicidal activity has been demonstrated with known flukicides including clorsulon and the benzimidazoles, such as albendazole, currently used for fluke control in ruminants. The flukicidal activity of the Formula I' pyrrole carbonitriles demonstrated by traditional in vivo methods has been shown by the in vitro screening method of the present invention.

Helminthiases is also caused by a group of worms referred to as nematodes. Nematodes cause serious damage to the walls and tissues of the organs in which they reside, including the intestinal tract, heart, lungs, and blood vessels, and are a primary cause of anemia. If left untreated they may result in death to the infected animals. The nematodes most commonly found to be the infecting agents of warm-blooded animals include Haemonchus, Ostertagia, Cooperia, Oesphagastomum, Nematodirus, and Dictyocaulus.

The nitropyrrole and carbonitrile compounds of the following formula are preferred for control of nematode infections and infestations:

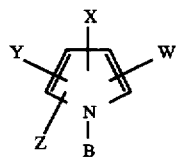

(I)

wherein

W is CN or $NO_2$;

X is CN, Br, Cl, I or $CF_3$;

Y is Br, Cl, I or $CF_3$;

Z is H, Br, Cl or I; and

B is hydrogen, $C_1$–$C_6$ alkyl optionally substituted with one to three halogen atoms, one cyano, one or two $C_1$–$C_4$ alkoxy groups optionally substituted with one to three halogen atoms, one phenyl optionally substituted with one to three halogen atoms, one to three $C_1$–$C_4$ alkyl groups or one to three $C_1$–$C_4$ alkoxy groups, one phenylcarbonyloxy group optionally substituted with one to three halogen atoms, one to three $C_1$–$C_4$ alkyl groups or one to three $C_1$–$C_4$ alkoxy groups, or one $C_1$–$C_6$ alkyloxycarbonyloxy group optionally substituted with one to three halogen atoms, $C_3$–$C_6$ alkenyl optionally substituted with one to three halogen atoms or one phenyl group, $C_3$–$C_6$ alkynyl optionally substituted with one to three halogen atoms or one phenyl group, or cyano.

Besides controlling helminths, the present invention also controls endoparasitic arthropod infestations such as cattle grub.

It has been further found that acarid and arthropod ectoparasitic infestations in warm-blooded animals such as lice, mange, ticks and fleas may be controlled, prevented or eliminated by the methods and compositions of the present invention.

For control of Acarina such as ticks and mites, including the mites responsible for causing mange, Psoroptes cuniculi, it has been found that the nitropyrrole or pyrrole carbonitrile compounds of the following structure are preferred:

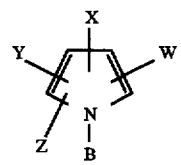

(I)

wherein

W is CN or $N_2$;

X is CN, Br, Cl, I or $CF_3$;

Y is H, Br, Cl, I or $CF_3$;

Z is H, Br, Cl or I; and

B is $$\overset{O}{\underset{}{\overset{\|}{C}}}R,$$

hydrogen, $C_1$–$C_6$ alkyl optionally substituted with one to three halogen atoms, one or two $C_1$–$C_4$ alkoxy groups optionally substituted with one to three halogen atoms, one phenyl optionally substituted with one to three halogen atoms, one to three $C_{1-4}$ alkyl groups or one to three $C_1$–$C_4$ alkoxy groups, one $C_1$–$C_6$ alkylcarbonyloxy group optionally substituted with one to three halogen atoms, one $C_1$–$C_6$ alkoxycarbonyl group optionally substituted with one to three halogen atoms or one to three $C_1$–$C_4$ alkoxy groups, or one $C_1$–$C_6$ alkyloxycarbonyloxy group optionally substituted with one to three halogen atoms, $C_3$–$C_6$ alkenyl optionally substituted with one to three halogen atoms or one phenyl group, $C_3$–$C_6$ alkynyl optionally substituted with one to three halogen atoms or one phenyl group, or $C_1$–$C_6$ alkyl substituted with one to three halogen atoms and one $C_1$–$C_4$ alkoxy group;

R is phenoxy optionally substituted with one to three halogen atoms, one or two $C_1$–$C_4$ alkyl groups, one or two $C_1$–$C_4$ alkoxy groups, $CF_3$, CN or $NO_2$, di($C_1$–$C_4$ alkyl)amino or $C_1$–$C_4$ alkanoylamino, $C_1$–$C_6$ alkoxy optionally substituted with one to three halogen atoms, or $C_2$–$C_6$ alkenyloxy optionally substituted with one to three halogen atoms.

Among the ticks which most often infest warm-blooded animals and poultry are members of the families Ixodidae, hard ticks, and Argasidae, soft ticks, including ticks of the genera Boophilus, Dermacentor, Rhipicephalus, Ixodes, Amblyomna, Otobius, Argas and Ornithodoros. The present invention has been found to be effective for controlling tick adults, larvae and nymphs.

The present invention has been found to be effective for controlling mites which are parasitic on warm-blooded mammals and poultry such as mites of the orders Acariformes and Parasitiformes, and particularly of the genera Otodectes, Psoroptes, Sarcoptes, Ornithonyssus, Demodex and Chorioptes.

The present invention is also effective for controlling arthropod ectoparasitic insects such as biting lice, sucking lice and fleas. Biting lice include members of Mallophaga such as *Bovicola bovis*, *Trichodectes canis*, and *Damilina ovis*. Sucking lice include members of Anoplura such as *Haematopinus eurysternus*, *Haematopinus suis*, *Linognathus vituli* and *Solenopotes capillatus*.

For the control of flea infestations, including fleas of the genera Ctenocephalides, Echidnophaga, Pulex and Xenopslla, the nitropyrrole or pyrrole carbonitrile compounds of the following structure are preferred:

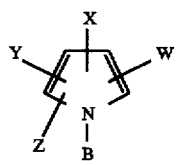

(I)

wherein

W is CN or $NO_2$;

X is CN, Br or Cl;

Y is H, Br or Cl;

Z is H, Br or Cl; and

B is hydrogen,
- $C_1$–$C_6$ alkyl optionally substituted with one to three halogen atoms,
  one or two $C_1$–$C_4$ alkoxy groups optionally substituted with one to three halogen atoms, or
  one $C_1$–$C_6$ alkyloxycarbonyloxy group optionally substituted with one to three halogen atoms,
- $C_3$–$C_6$ alkenyl optionally substituted with one to three halogen atoms or one phenyl group,
- $C_3$–$C_6$ alkynyl optionally substituted with one to three halogen atoms or one phenyl group,
- $C_3$–$C_6$ 1,2-alkadienyl, or cyano.

For control of flea infestations, treatment of the infested animal to control adults in conjunction with treatment of the area occupied by the infested animal to control flea larvae is recommended. The compositions of the present invention may be admixed with suitable carriers for application to interior and/or exterior areas for control of flea larvae.

It has been found that helminth, acarid and arthropod endo- and ectoparasitic infestations may be controlled, prevented or eliminated, by applying to, injecting or orally dosing said animals with an endo- or ectoparaslticidally effective amount of the above-described formula I and formula I′ pyrrole compounds. This may be achieved by applying the compound to the skin, hide and/or hair of the animals, or injecting or orally dosing said animals with a solid or liquid formulated composition.

The compositions of the present invention may be employed as animal feeds, animal feed premixes or feed concentrates. Feed concentrates and feed premixes, useful in the practice of the invention, may be prepared by admixing about 0.25% to 35% by weight of the formula I or formula I′ pyrrole compound with about 99.75% to 65% by weight of a suitable agronomic carrier or diluent. Carriers suitable for use include 0.75% to 35% by weight of a physiologically acceptable alcohol such as benzyl alcohol, phenethyl alcohol or propylene glycol, 0 to about 10% by weight of a vegetable oil such as corn oil or soybean oil, or propylene glycol and about 30% to 95% by weight of a sorptive, edible organic carrier such as corn grits, wheat middlings, soybean meal, expanded corn grits, extracted corn meal or the like or a sorptive silica or a silicate. These feed premixes or concentrates may be admixed with the appropriate amount of animal feed to provide the animals with about 0.5 ppm to 1000 ppm and preferably about 1 ppm to 500 ppm of the compound in the animal's diet. These premixes or concentrates may also be used as top dressings for the animal's daily ration and applied across the top of the daily ration in sufficient amount to provide the animal with about 0.5 ppm to 1000 ppm and preferably about 1 ppm to 500 ppm of the active ingredient, based on the animals total feed.

The formula I and formula I′ pyrrole compounds may be administered to the animals in or with their drinking water.

The compound may also be administered in the form of a pill, tablet, bolus, implant, capsule or drench, containing sufficient compound to provide the treated animal with about 0.01 mg/kg to 100 mg/kg of animal body weight per day of the compound. These dosage forms are prepared by intimately and uniformly mixing the active ingredient with suitable finely divided diluents, fillers, disintegrating agents and/or builders such as starch, lactose, talc, magnesium stearate, vegetable gums or the like. These unit dosage formulations may be varied with respect to the total weight and content compound depending upon the kind and size of the animal to be treated, the severity or type of infection encountered and the weight of the host.

Alternately, the compound may be administered to animals parenterally, for example, by intraruminal, intramuscular or subcutaneous injection in which even the active ingredient is dissolved or dispersed in a liquid carrier. For this type administration the compound may be dispersed in a physiologically acceptable solvent for subcutaneous injection or it may be dispersed in a fat or wax or mixture thereof containing an oil, buffer, surfactant, stabilizer, preservative and salt. Components useful in these preparations include carbowax, aluminum monostearate gel, diethyl succinate, soya oil, glyceral dioleate, saline and capric/caprylic triglycerides.

The formula I and formula I′ pyrrole compounds may also be applied topically to the larger animals such as swine, sheep, cattle and horses and companion animals such as dogs and cats in the form of aqueous dips or sprays. For this type administration, the active compound is generally prepared as a wettable powder, emulsifiable concentrate, aqueous flowable or the like, which is mixed with water at the site of treatment and applied topically to the hide, skin or hair of the animal. Such sprays or dips usually contain about 0.5 ppm to 5000 ppm and preferably about 1 ppm to 3000 ppm of the compound.

Advantageously, the formula I and formula I′ pyrrole compounds may also be prepared as pour-on formulations and poured on the backs of the animals such as swine, cattle, sheep, horses, poultry and companion animals to protect them against infestation by acarids and arthropod endo- and ectoparasites. Such pour-on compositions are generally prepared by dissolving, dispersing or emulsifying the formula I pyrrole compound in a suitable nontoxic pharmacologically acceptable diluent for pour-on and administration. The diluent must be compatible with the compound and should not be a source of irritation or damage to the animals hide, skin or hair. Such diluents include vegetable oils, spreading oils, polyhydric alcohols, aliphatic or aromatic hydrocarbons, esters of fatty acids and lower alkyl ketones.

A typical pour-on formulation includes about 0.5% to 30% by weight of the formula I or formula I' pyrrole compound, about 30% to 60% by weight of an aliphatic or aromatic hydrocarbon, mono or polyhydric alcohol, lower alkyl ketone or mixtures thereof, 0 to about 20% by weight of a vegetable or mineral oil and about 0.5% to 30% by weight of a spreading oil. Another typical pour-on contains about 45% by weight of xylene, about 15% by weight of the formula I pyrrole compound, about 10% by weight of corn oil or mineral oil, about 25% by weight of cyclohexanone and about 5% by weight of other pharmacologically acceptable spreading agents, antifoam agents surfactants or the like.

The formula I and formula I' pyrrole compounds may also be prepared as ear tags for animals, particularly quadrupeds such as cattle and sheep. The tags may be prepared by stirring together about 55% to 60% by weight of a vinyl dispersion resin, having an inherent viscosity of about 1.20 and an average particle size of about 0.75 microns, a curing temperature range of about 120° C. to 180° C., with about 28% by weight of butylbenzylphthalate. Stirring is continued, and about 1.5% by weight of ca/Zn stearate stabilizer is added along with about 7.0% of the compound and 2.8% of epoxidized soybean oil. The resulting mixture is deaerated for 15 to 20 minutes at 125 mm/Hg. The resulting can be coated on an ear tag blank by dipping and the resulting tag cured at about 145° to 150° C. for about five minutes.

The compounds useful in this invention may be prepared by several synthetic routes. For example, formula I halo substituted nitropyrroles, halo substituted pyrrole carbonitriles and halo substituted nitropyrrole carbonitriles may be prepared by halogenation of the appropriate nitropyrrole, pyrrole carbonitrile, pyrrole dicarbonitrile or nitropyrrole carbonitrile illustrated by formula II.

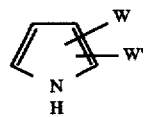
(II)

wherein W is CN or NO₂ and W' is hydrogen or CN.

Bromination of a formula II pyrrole is generally achieved by dissolution of the formula II pyrrole in a dilute aqueous base, such as aqueous sodium hydroxide, aqueous potassium hydroxide or the like, and treatment of the thus prepared reaction mixture with at least two to three equivalents of bromine. The reaction may be illustrated as follows:

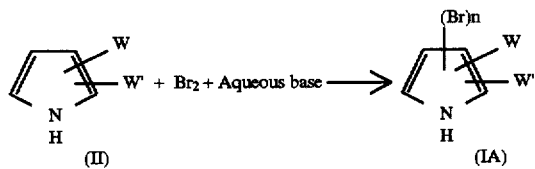

wherein W is CN or NO₂; W, is hydrogen or CN; and n represents the integer 3 when W' is hydrogen and the integer 2 when W' is CN. If desired, the thus prepared brominated nitropyrrole pyrrole mono- or dicarbonitrile or nitropyrrole carbonitrile, may be redissolved in dilute aqueous base and then acidified with a mineral acid such as hydrochloric acid, to obtain the brominated pyrrole or pyrrole carbonitrile in high purify.

It has also been found that bromination of a formula II pyrrole may be achieved by dissolving said formula II pyrrole in an organic solvent such as chloroform, methylene chloride, dioxane, tetrahydrofuran (THF) or the like, and admixing therewith bromine, or N-bromosuccinimide preferably dissolved in the same organic solvent employed for dissolution of the formula II pyrrole. Gentle warming of the reaction mixture may be employed to facilitate the bromination reaction.

Since the above reactions yield a variety of brominated nitropyrroles, brominated pyrrole mono- and dicarbonitriles and brominated nitropyrrole carbonitriles, that are formula I pyrroles by definition, but limited to brominated products, they are identified as group IA products in the reaction illustrated above.

Chlorination of a formula II pyrrole is readily achieved by reaction of the formula II pyrrole with about 2 to 3 equivalents of a chlorinating agent such as chlorine, sulfuryl chloride, or the like, in the presence of an organic acid, such as acetic or glacial acetic acid. When sulfuryl chloride is used, the reaction is generally conducted at a temperature below about 40° C. and preferably between 0° C. and 30° C. The reaction may be illustrated as follows:

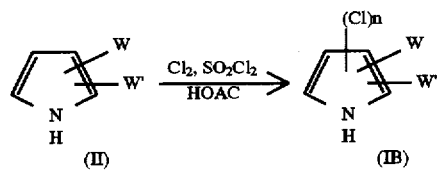

wherein W is CN or N₂; W' is hydrogen or CN and n represents the integer 3 when W' is hydrogen and integer 2 when W' is CN.

Chlorination of the formula II pyrrole may also be accomplished by reaction of said formula II pyrrole with t-butylhypochlorite or sodium hypochlorite in the presence of an inert organic solvent at reduced temperatures.

The group IB pyrroles, described in the above-reaction, are chlorinated nitropyrroles, chlorinated mono- and dicarbonitriles and chlorinated nitropyrrole carbonitriles, as defined by formula I but are limited to chlorinated products. As such, they are herein identified as group IB products.

Formation of the iodonitropyrroles, the di- and triiodopyrrole carbonitriles or the iodonitropyrrole carbonitriles may be achieved by iodination of an appropriately substituted formula III nitropyrrole carboxylic acid, mono- or dicyanopyrrole carboxylic acid or a cyano and nitro (substituted) pyrrole carboxylic acid dissolved in an aqueous solution of an alkali metal carbonate or bicarbonate. In this reaction the aqueous carbonate solution of the formula II pyrrole is treated with an aqueous solution of iodine and potassium iodide and then heated to a temperature of about 50° C. to 100° C. On cooling, the formula IC iodopyrrole is obtained. The reaction may be illustrated as follows:

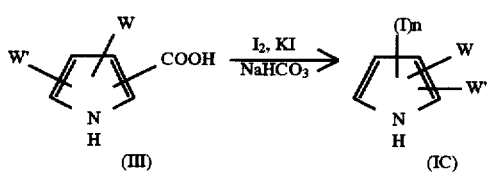

wherein W is CN or $N_2$; W' is hydrogen or CN; and n is the integer 3 when W' is hydrogen and the integer 2 when W' is CN.

Although the formula IC products, illustrated above, are all encompassed by the definition set forth for formula I, the above reaction provides only iodine substituted nitropyrroles, iodine substituted mono- or dicarbonitriles or iodine substituted nitropyrrole carbonitriles, thus the products of said reaction are designated by formula IC.

Formula I products in which X, Y, and or Y and Z are represented by two different halogen atoms may be prepared by first introducing one or two equivalents of a suitable halogenating agent into a formula II pyrrole followed by separation of the mono- or di-halogenated pyrrole and then adding an additional one or two equivalents of a second halogenating agent to give the formula I tetrasubstituted pyrrole.

Preparation of B-substituted formula I halonitropyrroles, halopyrrole carbonitriles and halonitropyrrole carbonitriles may be achieved by reaction of the appropriately substituted formula I pyrrole having B as hydrogen with an alkylating or acylating agent in the presence of an alkali metal alkoxide or hydride. More particularly, preparation of the B substituted formula I pyrrole involves reaction of formula I pyrrole:

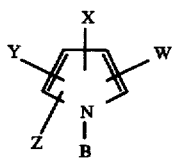

wherein B is hydrogen and W, X, Y and Z are as described in formula I above, with an appropriate alkylating agent such as a $C_1$–$C_6$ alkylhalide in which the alkyl group is straight or branched and is optionally substituted with from one to three halogen atoms, one hydroxy, one cyano, one $C_1$–$C_4$ alkoxy, one $C_1$–$C_4$ alkylthio, one phenyl group, optionally substituted with from one to three halogen atoms, or one benzyloxy group, optionally substituted with from one to three halogen atoms, and an alkali metal alkoxide such as sodium or potassium t-butoxide. This reaction provides a halo nitropyrrole, halopyrrole (mono- or di) carbonitrile or halonitropyrrole carbonitrile having the same substituents as the starting material, but in addition is substituted on the nitrogen with a $C_1$–$C_6$ alkyl group optionally substituted as described above. The reaction may be illustrated as follows:

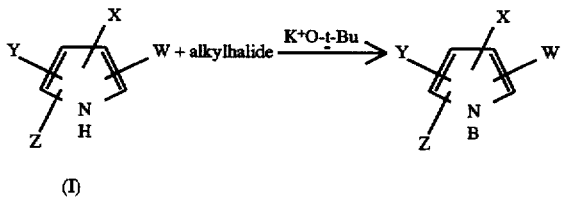

In a similar reaction cyanogen bromide is substituted for the alkylhalide and yields the formula I halo substituted nitropyrrole, halopyrrole carbonitrile or halonitropyrrole carbonitrile having a carbonitrile, rather than an alkyl group, on the nitrogen. Formula IA, IB and IC compounds may also be alkylated in accordance with the above procedure by substituting a compound according to formula IA, IB or IC for the formula I pyrrole in which W, X, Y and Z represent substituents as described above and B is hydrogen.

Advantageously, the above-described alkylation procedure of the formula I, IA, IB and IC, halo (substituted) pyrroles, in which B is hydrogen, may also be applied to the preparation of formula I halopyrroles having an N-$C_3$-$C_6$ alkenyl or N-$C_3$-$C_6$ alkynyl substituent. This N-substitution may be obtained by simply substituting a $C_3$-$C_6$ alkenyl halide or $C_3$-$C_6$ alkynyl halide for the $C_1$-$C_6$ alkyl halide in the above-described reaction.

In a similar manner, preparation of N-acylated halonitropyrroles, halopyrrole carbonitriles and halonitro pyrrole carbonitriles may be achieved by the reaction of an appropriately substituted formula I pyrrole wherein B is hydrogen with an acylating agent in the presence of an alkalai metal alkoxide. Acylating agents such as $C_1$-$C_6$ alkyl or $C_2$-$C_6$ alkenyl acid chloride, substituted $C_1$-$C_6$ alkyl or $C_2$-$C_6$ alkenyl acid chloride, benzoyl chloride, substituted benzoyl chloride, phenylchloroformate, substituted phenylchloroformate, $C_1$-$C_6$ alkyl or $C_2$-$C_6$ alkenylchloroformate, substituted $C_1$-$C_6$ alkyl or $C_2$-$C_6$ alkenylchloroformate, N-substituted carbamoyl chloride and the like may be employed. The reaction may be illustrated as follows:

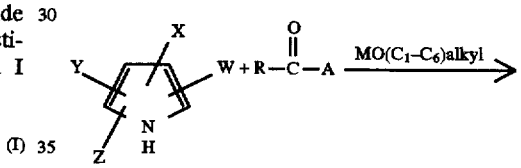

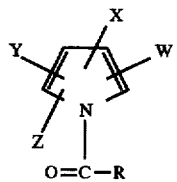

wherein A is halogen, M is alkalai metal and W, X, Y, Z and R are as described hereinabove for formula I.

Preparation of (trifluoromethyl)pyrrole carbonitriles and conversion thereof to dihalo (trifluoromethyl)pyrrole carbonitriles and dihalo- alkylated N-(trifluoromethyl)pyrrole carbonitriles can be achieved by the admixture of a dispersion of sodium hydride in tetrahydrofuran with a solution of ethyl trifluoroacetate and 3-cyano propionaldehyde diethyl acetal in tetrahydrofuran. The reaction that occurs yields 3-trifluroacetyl-3-cyanopropionaldehyde diethyl acetal which is then heated with oxalic acid dihydrate in water to give the 3-trifluoroacetyl-3-cyanopropionaldehyde. The thus prepared aldehyde is then dissolved in glacial acetic acid and the resulting solution treated with ammonium acetate to provide the 2-(trifluoromethyl)pyrrole-3-carbonitrile. Halogenation of the above-said (trifluoromethyl)pyrrole carbonitrile may then be accomplished by reaction of said (trifluoromethyl)pyrrole carbonitrile with N-bromosuccinimide or N-chlorosuccinimide in the presence of tetrahydrofuran to yield the dihalo (trifluoromethyl) pyrrole carbonitrile. Alkylation or acylation of this dihalo (trifluoromethyl)pyrrole carbonitrile with an alkyl halide or acylhalide in the presence of potassium t-butoxide and tetrahydrofuran yields the N-alkylated (or N-acylated) dihalo (trifluoromethyl)pyrrole carbonitrile.

Other methods for the preparation of the formula I halo substituted nitropyrroles, halo substituted pyrrole carbonitriles, halo substituted nitropyrrole carbonitriles and the N-substituted derivatives thereof, will become apparent from the examples set forth below.

The formula I, pyrrole carbonitriles are prepared similarly to the formula I compounds as set forth herein.

EXAMPLE 1

Evaluation of test compounds as nematocidal agents

Cultures of *C. elegans* (Bristol strain from J. Lewis) are maintained on *E. coli* lawns on NG Agar Plates at 20° C. New cultures are established weekly.

Nematodes for testing are washed from 4–5 day old cultures using Ringers Solution.

Compounds are dissolved in acetone and made up to volume with equal parts of water. The final test concentration of each compound is 150 ppm. The test material is micropipetted (25 ul) into a single well of a 96-well sterile tissue culture plate and the solvent allowed to evaporate. These "treated" plates are used immediately or stored in a freezer without apparent adverse effects on the compounds.

A freshly prepared volume (50 µl) of *C. elegans* in Ringers Solution is micropipetted into each treated well and several control wells per plate. Culture plate are incubated at 20° C.

Observations for efficacy are made under a dissecting microscope at 4 and 24 hours post-immersion. Immediately prior to reading the plate, it is gently tapped to stimulate the movement of the worms. Activity is judged subjectively, but semi-quantitatively, based on the drug effects on motility of the adults and larvae. The criteria are as follows: 9=complete kill, 8=no motility, 7=markedly reduced motility in approximately 95% of worms and 0=normal motility, same as controls. Other factors indicating activity are easily noted such as death, rigor mortis, contraction, coiling, paralysis, abnormal twitching, reduced worm population and other deviation from normal behavior.

| PROCEDURE FOR *CAENORHABDITIS ELEGANS* ASSAY | |
|---|---|
| Day 0 | Inoculate *E. Coli*-NG Agar Dish With 30–40 *C. Elegans* Incubate At 20° C. |
| Day 4 | Harvest New *C. Elegans* Population Add *C. Elegans* (50 UL) To "Medicated" Wells* Observe for Activity at 4 hours Post-Immersion |
| Day 5 | Observe For Activity |

*Medicated Wells May Be Prepared Fresh or Earlier and Stored In Freezer

Data obtained in these tests are reported in Table I below.

TABLE I

Evaluation of Formula I Pyrrole Activity Against *C. Elegans*

| Formula I Compound | Rating Against *C. Elegans* 150 ppm |
|---|---|
| 2-Chloro-4-nitropyrrole | 9 |
| 2,5-Dichloro-3-nitropyrrole | 9 |
| 2,3-Dichloro-4-nitropyrrole | 9 |

TABLE I-continued

Evaluation of Formula I Pyrrole Activity Against *C. Elegans*

| Formula I Compound | Rating Against *C. Elegans* 150 ppm |
|---|---|
| 2,3,5-Trichloro-4-nitropyrrole | 9 |
| 2,5-Dibromo-3-nitropyrrole | 9 |
| 2,3-Dibromo-4-nitropyrrole | 9 |
| 2,4,5-Trichloropyrrole-3-carbonitrile | 9 |
| 4,5-Dichloropyrrole-3-carbonitrile | 9 |
| 2,4,5-Tribromopyrrole-3-carbonitrile | 9 |
| 2,4,5-Trichloro-1-methylpyrrole-carbonitrile | 9 |
| 2,4,5-Tribromo-1-methylpyrrole-carbonitrile | 9 |
| 2,4,5-Tribromopyrrole-1,3-di-carbonitrile | 9 |
| 4,5-Dibromopyrrole-2-carbonitrile | 9 |
| 3,4,5-Tribromopyrrole-2-carbonitrile | 9 |
| 3,4,5-Tribromopyrrole-2-carbonitrile | 9 |
| 3,4,5-Tribromo-1-methylpyrrole-2-carbonitrile | 9 |
| 2,5-Diiodo-1-methylpyrrole-3-carbonitrile | 9 |
| 5-Nitropyrrole-5-carbonitrile | 9 |
| 4-Nitropyrrole-2-carbonitrile | 9 |
| 3,4-Dibromo-5-nitropyrrole-2-carbonitrile | 9 |
| 3,5-Dibromo-4-nitropyrrole-2-carbonitrile | 9 |
| 1-(Ethoxymethyl)-5-nitropyrrole-2-carbonitrile | 9 |
| 1-Allyl-2,4,5-Tribomopyrrole-3-carbonitrile | 9 |
| 4,5-Dibromo-1-(ethoxymethyl)-2-(trifluoromethyl)pyrrole-3-carbonitrile | 9 |

EXAMPLE 2

Evaluation of nitropyrroles and pyrrole carbonitriles against *Ctenocephalides felis*, the cat flea On the day prior to the test initiation the drugs to be evaluated are dissolved in acetone and diluted to the desired concentrations. The concentration is calculated so that 400 µl contains the amount of test compound to be placed on each filter paper. 400 µl of this solution is pipetted onto a (3.7 cm diameter) filter paper disk which is then placed on a ceramic plate to dry. There is a rough and smooth side to the filter paper. Drug should be applied to the rough side to the filter paper and placed up while drying. When dry, the disk is placed in a Petri dish with the rough side facing up and then held at room temperature overnight if done the day before the test.

(1) Unfed fleas that have emerged from pupae within the last 24 hours are used for the test. Fleas are initially collected in glass vials and then temporarily immobilized by placing the vials in ice. Once the fleas are no longer active, vials are opened and fleas dumped into Petri dishes. The number of fleas per dish will vary but generally will be 8–12 fleas.

(2) Edges of the Petri dish are sealed with Scotch tape to prevent escape of the fleas.

(3) Dishes are held for 24 hours before the mortality counts are made.

(4) Dishes are not opened when the test is read but fleas in the dishes are observed under dissecting scope.

15

Some fleas will move under the filter paper so the dish should be inverted to check. Fleas are considered dead if they cannot remain upright and jump.

(5) Percent mortality of the fleas, corrected for control mortality, is then calculated for each treatment.

Data obtained are reported in Table II below.

TABLE II

Evaluation of nitropyrroles and pyrrole carbonitriles against *Ctenocephalides felis*, the cat flea

| Compound | µg/cm² | 24 hour % Mortality |
|---|---|---|
| 2,4,5-Tribromo-1-methyl-pyrrole-3-carbonitrile | 10 | 100 |
|  | 1 | 100 |
| 4,5-Dibromo-1-methylpyrrole-2-carbonitrile | 10 | 100 |
|  | 1 | 10 |
| 3,4,5-Tribromo-1-methyl-pyrrole-2-carbonitrile | 10 | 100 |
|  | 1 | 100 |
| 3,4,5-Tribromo-1-(2-pro-pynyl)-pyrrole-2-carbo-nitrile | 10 | 100 |
|  | 1 | 100 |
| 3,4,5-Tribromopyrrole-2-carbonitrile | 10 | 100 |
| 4,5-Dibromopyrrole-2-carbonitrile | 10 | 100 |
|  | 1 | 100 |
| 2,3,5-Trichloro-1-methyl-pyrrole-3-carbonitrile | 10 | 97 |
| 2,4,5-Tribromo-1-(2-pro-pynyl)-pyrrole-3-carbo-nitrile | 10 | 92 |
| 3,5-Dibromo-1-methyl-pyrrole-2,3-dicarbonitrile | 10 | 18 |
| 2,4,5-Tribromopyrrole-1,3-dicarbonitrile | 10 | 98.5 avg. 2 reps. |
| 3,4,5-Tribromo-1-(1,2-propadienyl)pyrrole-2-carbonitrile | 10 | 100 |
|  | 1 | 100 |
| 2-Bromo-1-methyl-4-nitropyrrole | 10 | 100 |
| 2,4,5-Tribromo-1-(methoxymethyl)pyrrole-3-carbonitrile | 10 | 100 |
|  | 1 | 100 |

EXAMPLE 3

Evaluation of nitropyrroles and pyrrole carbonitriles against *Psoroptes cuniculi*

On the day prior to the test initiation the drugs to be evaluated are dissolved in acetone and diluted to the desired concentrations. The concentration is calculated so that 400 µl contains the amount of test compound to be placed on each filter paper. 400 µl of this solution is pipetted onto top (3.7 cm dia.) and bottom (3.5 cm dia.) filter paper disks which are then placed on a ceramic plate to dry. There is a rough and smooth side to the filter paper. Drug should be applied to the rough side which is placed up while drying. When dry the two disks are placed in a Petri dish with the rough sides facing in, separated by one 3 mm glass bead. Dishes are held at room temperature overnight if prepared the day before the test.

Scab (containing mites) is collected from the ears of infested rabbits the morning of the test. This material is placed in a large Petri dish under an illuminated magnifier. Mites crawl out of the scab and are easily collected on the point of a dissecting needle or one prong of a pair of fine forceps. The top filter paper in each dish is removed and 12 mites are placed on the bottom disk and the top paper replaced. Before replacing the top of the Petri dish the rim of the dish is smeared with petroleum jelly to trap any escaping mites. After mites are added to the dishes, the dishes in each replicate are placed in a tray which is then placed in a plastic bag with several wet towels and held at room temperature.

16

For evaluation tests there are generally 4 replicates of each dose which are counted at 24 hours. After 24 hours the dishes are examined under a dissecting scope. Each dish is opened carefully and the top filter paper removed and saved. A ½ cm circle is drawn on the bottom filter paper and the paper gently wet in the area of the circle. All mites from the dish and top filter paper are transferred into the wet circle area and counted. The top cover is replaced on each dish and the dishes set aside for at least 15 minutes. After standing the dishes are examined and the mites remaining in the circle counted. These mites are dead. Percent mortality of the mites, corrected for control mortality, is then calculated for each treatment. These data are reported in Table III below.

TABLE III

Evaluation of nitropyrroles and pyrrole carbonitriles against *Psoroptes cuniculi* (Rabbit Ear Mite)

| Compound | µg/cm² | 24 hour % Mortality |
|---|---|---|
| 4,5-Dibromopyrrole-2-carbonitrile | 4 | 100 |
|  | 1 | 100 |
| 3,4,5-Tribromo-1-methyl-pyrrole-2-carbonitrile | 4 | 100 |
|  | 1 | 58 |
| 2,5-Diiodo-1-methyl-pyrrole-3-carbonitrile | 4 | 100 |
|  | 1 | 100 |
| 2,4,5-Tribromo-1-methyl-pyrrole-3-carbonitrile | 4 | 14 |
| 2,4,5-Tribromo-1-(ethoxy-methyl)pyrrole-3-carbonitrile | 4 | 54 |
| 3,4,5-Tribromopyrrole-2-carbonitrile | 4 | 100 |
|  | 1 | 89 |
| Pyrrole-3,4-dicarbonitrile | 4 | 12 |
| 4-Nitropyrrole-2-carbonitrile | 4 | 44 |
| 1-Methyl-5-nitropyrrole-2-carbonitrile | 4 | 92 |
| 1-Allyl-2,4,5-tribromopyrrole-3-carbonitrile | 4 | 37 |
| 3,4,5-Tribromo-1-(2-propynyl)-pyrrole-2-carbonitrile | 4 | 100 |
|  | 1 | 100 |
| 4,5-Dibromo-2-(trifluoro-methyl)pyrrole-3-carbonitrile | 4 | 11 |
| 4,5-Dibromo-1-methylpyrrole-3-carbonitrile | 4 | 100 |
| 4,5-Dibromo-1-(ethoxymethyl)-2-(trifluoromethyl)pyrrole-3-carbonitrile | 4 | 100 |
| 2,4,5-Tribromo-1-(hydroxy-methyl)pyrrole-3-carbonitrile, pivalate (ester) | 4 | 100 |
|  | 1 | 86 |
| 2,4,5-Tribromo-1-(3,4-dichloro-benzyl)pyrrole-3-carbonitrile | 4 | 100 |
|  | 1 | 19 |
| tert-Butyl 2,3,5-tribromo-4-cyanopyrrole-1-acetate | 4 | 5 |
| 2,4,5-Tribromo-1-(isopropoxy-methyl)pyrrole-3-carbonitrile | 4 | 100 |
| 2,4,5-Tribromo-1-(2-chloro-1-ethoxyethyl)pyrrole-3-carbo-nitrile | 4 | 100 |
|  | 1 | 100 |
| 2,4,5-Tribromo-1-(hydroxy-methyl)pyrrole-3-carbonitrile, acetate (ester) | 4 | 91 |
| Ethyl 1-(2,3,5-tribromo-4-cyanopyrrol-1-yl)ethylcarbonate | 4 | 100 |
|  | 1 | 46 |
| Phenyl 2,3,5-tribromo-4-cyanopyrrole-1-carboxylate | 4 | 41 |
| 2,4,5-Tribromo-1-(methoxy-methyl)pyrrole-3-carbonitrile | 4 | 100 |
|  | 1 | 95 |

EXAMPLE 4

Evaluation of test compounds against the newly hatched larvae of the Dogtick, *Dermacentor variabilis*

The test procedure used herein is the same procedure described in New Example 3, for evaluating test compounds for control of *Psoroptes cuniculi* the Rabbit Ear Mite, with the following exceptions:

(1) Unfed larval ticks are obtained from egg masses laid by gravid female ticks removed from dogs and each replicate receives ticks from the same egg mass; and (2) When reading the test it may be necessary to blow on the ticks to stimulate their movement.

Data obtained are reported in Table IV below.

TABLE IV

Evaluation of Formula I pyrroles against the larval stage of the Dogtick, *Dermacentor variabilis*

| Formula I Compound | μg/cm² | 24 hour % Mortality |
|---|---|---|
| 2,4,5-Tribromopyrrole-3-carbonitrile | 10 | 95 |
| 2,4,5-Tribromo-1-methyl-pyrrole-3-carbonitrile | 10 | 100 |
|  | 1 | 82 |
| 2,4,5-Tribromo-1-(ethoxy-methyl)pyrrole-3-carbonitrile | 1 | 5 |
| 4,5-Dibromopyrrole-2-carbonitrile | 10 | 100 |
|  | 5 | 100 |
|  | 1 | 100 |
| 3,4,5-Tribromo-1-methyl-pyrrole-2-carbonitrile | 10 | 90 |
| 2,5-Diiodo-1-methyl-pyrrole-3-carbonitrile | 10 | 100 |
|  | 5 | 100 |
|  | 1 | 75 |
| 3,4,5-Tribromo-1-(2-propynyl)pyrrole-2-carbonitrile | 10 | 100 |
|  | 5 | 100 |
|  | 1 | 69 |
| 2,4,5-Tribromo-1-(hydroxy-methyl)pyrrole-3-carbonitrile, pivalate (ester) | 10 | 100 |
| 2,4,5-Tribromo-1-(isopropoxymethyl)pyrrole-3-carbonitrile | 10 | 95 |
| Allyl 2,3,5-tribromo-4-cyanopyrrole-1-carboxylate | 10 | 100 |
|  | 5 | 94 |
| 2,4,5-Tribromo-1-(methoxy-methyl)pyrrole-3-carbonitrile | 10 | 100 |
|  | 1 | 74 |

EXAMPLE 5

Evaluation of test compounds against *Dugesia tigrina* and *Phagocata morgani* (Planaria)

The flukicidal activity of test compounds is demonstrated in the following tests. Test compounds are administered to gerbils in the diet, by a single oral gavage dose or by a single subcutaneous injection at the dosage indicated. After 4 days of feeding or 2–24 hours post-treatment in the case of oral gavage or subcutaneous administration, the gerbils are sacrificed and their livers are removed. Frozen liver which has been thawed, or fresh liver, is then fed to individual planaria in small dishes containing sterilized pond water. The planaria are observed to see if feeding occurs. Livers are removed after 2–4 hours. Planaria are then observed for 3–4 days and their activity is compared to controls fed liver from untreated gerbils. Toxicity is demonstrated by death and unnatural activity such as rapid movement, writhing or floating on the surface. Data obtained are reported in Table V below. The rating system employed is as follows:

| Rating System |
|---|
| + = Toxic effect observed |
| ± = Possible toxic effect observed |
| 0 = No toxic effect observed |
| — = Not tested |

TABLE V

Evaluation of compounds against *Dugesia tigrina* and *Phagocata morgani* (Planaria)

| Compound | PPM in Diet | Efficacy Dugesia tigrina | Efficacy Phagocata morgani |
|---|---|---|---|
| 2,4,5-Tribromopyrrole-3-carbonitrile | 20 | — | 0 |
|  | 50 | — | 0 |
|  | 100 | — | ± |
|  | Single oral dose 10 mg/kg, sacrificed 5.5 hr post-administration | 0 | ± |
| 2,4,5-Tribromo-1-methyl-pyrrole-3-carbonitrile | 10 | 0 | 0 |
|  | 50 | 0 | 0 |
|  | 100 | ± | 0 |
| 2,4,5-Tribromo-1-(ethoxy-methyl)pyrrole-3-carbonitrile | 100 | ± | — |
| 2,4,5-Tribromo-1-ethyl-pyrrole-3-carbonitrile | 100 | 0 | 0 |
|  | Single oral dose 10 mg/kg, sacrificed 5.5 hr post-administration | — | + |
| 1-Allyl-2,4,5-tribromo-pyrrole-3-carbonitrile | 100 | 0 | 0 |
| 2,4,5-Tribromo-1-(hydroxy-methyl)pyrrole-3-carbonitrile | 20 | — | 0 |
|  | 50 | — | ± |

TABLE V-continued

Evaluation of compounds against *Duqesia tigrina* and *Phagocata morgani* (Planaria)

| Compound | PPM in Diet | Efficacy | |
|---|---|---|---|
| | | *Duqesia tigrina* | *Phaqocata morgani* |
| nitrile, pivalate (ester) | 100 | + | ± |
| | Single subcutaneous injections 10 mg/kg, sacrificed 2 hr post-administration | + | — |
| 2,4,5-Tribromo-1-(isopropoxymethyl)pyrrole-3-carbonitrile | 100 | ± | + |
| | Single oral dose 10 mg/kg, sacrificed 8 hr post-administration | — | 0 |
| 2,4,5-Tribromo-1-(p-chlorophenacyl)pyrrole-3-carbonitrile | 500 | — | 0 |
| 2,4,5-Tribromo-1-[(trimethylsilyl)methyl]-pyrrole-3-carbonitrile | 500 | 0 | — |
| 2,4,5-Tribromo-1-(2-chloro-1-ethoxyethyl)-pyrrole-3-carbonitrile | 100 | ± | — |
| | 500 | ± | 31 |
| 2,4,5-Tribromo-1-(hydroxymethyl)pyrrole-3-carbonitrile, acetate (ester) | 100 | ± | — |
| | 500 | ± | — |
| Ethyl 1-(2,3,5-tribromo-4-cyanopyrrol-1-yl)ethyl-carbonate | 100 | — | 0 |
| | 500 | ± | — |
| 2,4,5-Tribromo-1-(p-chlorobenzoyl)pyrrole-3-carbonitrile | 100 | 0 | + |
| | 250 | 0 | + |
| | Single oral dose 10 mg/kg, sacrificed 6 hr post-administration | 0 | + |
| Phenyl 2,3,5-tribromo-4-cyanopyrrole-1-carboxylate | 100 | 0 | — |
| 2,4,5-Tribromo-1-(p-chlorobenzyl)pyrrole-3-carbonitrile | 100 | — | ± |
| 2,4,5-Tribromo-1-(hydroxymethyl)pyrrole-3-carbonitrile, benzoate (ester) | 100 | — | 0 |
| Methyl 2,3,5-tribromo-4-cyanopyrrole-1-carboxylate | 100 | — | + |
| Vinyl 2,3,5-tribromo-4-cyanopyrrole-1-carboxylate | 100 | ± | — |
| 3,4,5-Tribromo-1-(2-chloro-1-ethoxyethyl)pyrrole-2-carbonitrile | 100 | 0 | — |
| 3,4,5-Tribromo-1-(ethoxymethyl)pyrrole-2-carbonitrile | 100 | — | 0 |
| 2,4,5-Tribromo-1-(p-methoxybenzoyl)pyrrole-3-carbonitrile | 500 | ± | + |
| Allyl 2,3,5-tribromo-4-cyanopyrrole-1-carboxylate | 100 | + | ± |
| | Single oral dose 10 mg/kg, sacrificed 8 hr post-administration | + | — |
| | 10 mg/kg, sacrificed 24 hr post-administration | — | + |
| | Single subcutaneous injection 10 mg/kg, sacrificed 24 hr post-administration | — | ± |
| (2,3,4-Tribromo-5-cyano-pyrrol-1-yl)methyl pivalate | 500 | 0 | 0 |
| 2,5-Dibromo-1-(ethoxymethyl)-4-(trifluoromethyl)-pyrrole-3-carbonitrile | 25 | — | 0 |
| 2,5-Dibromo-1-(2-chloro-1-ethoxyethyl)-4-(trifluoromethyl)pyrrole-3-carbonitrile | 100 | + | — |
| 2,4,5-Tribromo-1-pivaloyl-pyrrole-3-carbonitrile | 500 | 0 | — |
| 2,5-Dibromopyrrole-3,4-dicarbonitrile | 500 | — | 0 |
| 2,4,5-Tribromo-1-(methoxy- | 50 | — | + |

TABLE V-continued

Evaluation of compounds against *Duqesia tigrina* and *Phaqocata morgani* (Planaria)

| Compound | PPM in Diet | Efficacy Duqesia tigrina | Efficacy Phaqocata morgani |
|---|---|---|---|
| methyl)pyrrole-3-carbonitrile | 100 | — | + |
|  | 500 | 0 | + |
| 2,5-Dibromo-1-methyl-pyrrole-3,4-dicarbonitrile | 500 | 0 | ± |
| 2,4,5-Tribromo-1-(bromomethyl)pyrrole-3-carbonitrile | 100 | — | 0 |
| 2,5-Dibromo-1-(ethoxymethyl)pyrrole-3,4-dicarbonitrile | 500 | 0 | 0 |
| 2,4,5-Tribromo-1-(chloromethyl)pyrrole-3-carbonitrile | 250 | — | ± |
|  | 500 | ± | + |
|  | Single oral dose |  |  |
|  | 50 mg/kg, sacrificed 6 hr post-administration | 0 | ± |
|  | 50 mg/kg, sacrificed 2 hr post-administration | — | 0 |
| 4,5-Dibromo-1-(tert-butoxymethyl)pyrrole-3-carbonitrile | 500 | — | 0 |
| Albendazole | Single oral dose | + | ± |
|  | 100 mg/kg, sacrificed 8 hr post-administration |  |  |
| Clorsulon | 100 | — | + |
|  | 25 | — | + |

EXAMPLE 6

Evaluation of test compounds against *Faciola hepatica* (Liver Fluke)

Female Wistar rats are infected with 20 *Faciola hepatica* metacercariae and allocated to 22 test groups of 10 rats each. Each group of rats is treated by oral gavage or by subcutaneous injection with a single dose of test compound at the dosage indicated, at 2, 10 or 12 weeks post-infection. Four groups of 12 untreated rats infected with 20 *Faciola hepatica* metacercariae serve as the control. Feed and water are offered ad libitum. Each group of rats is sacrificed at 12 or 14 weeks post-infection and examined for flukes. The number of flukes recovered from treated rats is compared with the number recovered from infected untreated controls. The data obtained are reported in Table VI below.

TABLE VI

Evaluation of Formula I' Compounds Against *Fasciola hepatica* (Liver Fluke)

| Formula I' Compound | Oral Dose mg/kg | % Fluke Reduction Treatment Week/Sacrifice Week | | | |
|---|---|---|---|---|---|
|  |  | 2/12 | 2/14 | 10/12 | 12/14 |
| 2,4,5-Tribromo-1-(hydroxymethyl)-pyrrole-3-carbonitrile pivalate (ester) | 25 | 100 | 88 | 92 | 100 |
|  | 8.3 Subcutaneous Injection | 90 | — | 100 | — |
|  | 10 | 95 | — | — | — |
|  | 5 | — | — | 71 | — |
| 2,4,5-Tribromo-1-methyl-pyrrole-3-carbonitrile | 20 | 93 | — | — | — |
|  | 12 | — | — | 100 | — |
|  | 6.7 | 92 | — | — | — |
|  | 4 | — | — | 85 | — |
| 2,4,5-Tribromo-1- | 10 | 92 | — | 90 | — |

TABLE VI-continued

Evaluation of Formula I' Compounds Against *Fasciola hepatica* (Liver Fluke)

| Formula I' Compound | Oral Dose mg/kg | % Fluke Reduction Treatment Week/Sacrifice Week | | | |
|---|---|---|---|---|---|
|  |  | 2/12 | 2/14 | 10/12 | 12/14 |
| (methoxymethyl)-pyrrole-3-carbonitrile | 3.3 | 53 | — | 85 | — |
| 2,4,5-Tribromo-1-(isopropoxymethyl)-pyrrole-3-carbonitrile | 10 | — | 80 | — | 100 |
| 2,4,5-Tribromo-1-(p-chlorobenzoyl)-pyrrole-3-carbonitrile | 10 | — | 80 | — | 100 |
| Allyl 2,3,5-tribromo-4-cyano-pyrrole-1-carboxylate | 10 | — | 90 | — | 100 |

EXAMPLE 7

Evaluation of test compounds for control of Nematodes in warm-blooded animals

Each test generally consists of 75 infected gerbils, randomly distributed a or 3 per cage (the number of animals per cage is consistent within a specific experiment). Generally, there are 8–9 untreated control gerbils (3–4 cages) per test. The remaining cages are assigned a treatment, usually 1 cage per compound or dose.

Compounds administered in diet are fed for 4 days. Animals treated by gavage or injection are generally treated on day 7.

In accordance with this test, gerbils are each orally infected by gavage, with about 400 *Trichostrongylus colubriformis* infective larvae of sheep origin. The infected animals are then permitted to feed and drink ad libitum for six days. On day 7 the infected gerbils are randomly placed in rodent cages, 2 or 3 animals per cage. The animals in each cage are weighed and the feed for each cage weighed. If the treatment to be evaluated is medicated feed, said medicated feed is offered on day 7 and continued through day 11 of the trial. If the treatment to be evaluated is a single oral dose or a parenteral treatment, the animals are given the medication by gavage or injection on day 7 and receive unmedicated feed and water through day 11 of the trial. On day 11 the animals and their feed are weighed. Thereafter the animals are euthanized by $CO_2$ inhalation and their small intestines removed, inverted on application sticks and incubated in tap water at 39° C. for 1.5 hours. The sticks and intestines are then discarded and the worms from each treatment counted to determine the % mortality of the worms as compared to untreated controls. Data obtained are reported in Table VII below.

TABLE VII

Evaluation of Formula I compounds against *T. colubriformis* in Gerbils

| Formula I Compound | PPM in Diet | % Nematode removal |
|---|---|---|
| 2,4,5-Trichloro-1-methyl-pyrrole-3-carbonitrile | 50 | 51 |
| 2,4,5-Tribromo-1-methyl-pyrrole-3-carbonitrile | 100 | 18 |
| 2,4,5-Tribromopyrrole-1,3-dicarbonitrile | 100 | 54 |
| 4,5-Dibromo-1-methylpyrrole-2-carbonitrile | 500 | 25 |
| 3,4,5-Tribromopyrrole-2-carbonitrile | 125 | 31 |
| 4,5-Dibromopyrrole-2-carbonitrile | 500 | 6 |
| 3,4,5-Tribromo-1-(2-propynyl)pyrrole-2-carbonitrile | 500 | 9 |

EXAMPLE 8

Preparation of 1-Methyl-5-nitropyrrole-2-carbonitrile

To a solution of 300 mg of 5-nitropyrrole-2-carbonitrile (2.14 mmol) in 15 mL of acetone, 360 mg of potassium carbonate (2.6 mmol) and 0.165 mL of iodomethane (2.6 mmol, 372 mg) are added. The mixture is then stirred at room temperature for 24 hours. The reaction mixture is poured into ice-water (100 mL) and the precipitate which forms is collected to yield (200 mg), 62%; mp 86°–87° C. of 1-methyl-5-nitropyrrole-2-carbonitrile.

EXAMPLE 9

Preparation of 1-Ethoxymethyl-5-nitropyrrole-2-carbonitrile

To a solution of 560 mg of 5-nitropyrrole-2-carbonitrile (4 mmol) in 20 mL of dry THF, is added 515 mg of potassium tert-butoxide (4.6 mmol). After the addition of 0.45 mL of chloromethylethylether (4.8 mmol) to the mixture, the mixture is stirred for 4 hours, then diluted with ether (30 mL) and water (50 mL). The organic layer is separated, washed with water $MgSO_4$ (20 mL) and dried over $MgSO_4$. After evaporation of the solvent a red oil is obtained (600 mg, 75%) 1-(ethoxymethyl)-5-nitropyrrole-2-carbonitrile. Anal.

Calcd: C, 49.23%; H, 4.65%; N, 21.53%. Found: C, 49.40%; H, 4.07%; N, 21.30%.

EXAMPLE 10

Preparation of 3-Trifluoroacetyl-3-cyanopropionaldehyde diethyl acetal

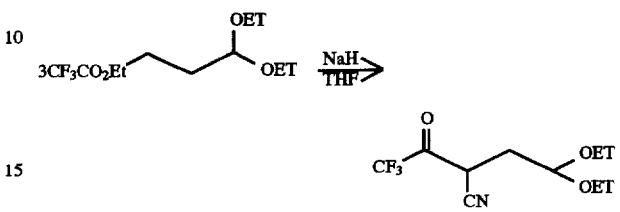

To a 40°–45° C. stirring suspension of hexane-washed sodium hydride (5.5 g of a 60% dispersion, 0.14 mol) in 200 mL of dried tetrahydrofuran is added dropwise a solution of ethyl trifluoroacetate (15 g, 0.11 mol) and 3-cyanopropionaldehyde diethyl acetal (17 g, 0.11 mol) in 100 mL of dry tetrahydrofuran. The previously gray suspension slowly turns light brown in color. The reaction mixture is stirred at 50°–55° C. overnight before being quenched by slow addition of 2-propanol (15 mL). Rotary evaporation of the volatiles yields a dark oil, to which is added 150 mL of pH 7 water. Unreacted starting materials are conveniently removed by washing the aqueous layer with diethyl ether (3×30 mL). The basic aqueous phase is then acidified with 12N hydrochloric acid and extracted with ethyl acetate (2×100 mL). The combined organic layers are washed once with saturated sodium bicarbonate (40 mL) and once with brine (15 mL) before being dried over magnesium sulfate. Rotary evaporation yields a reddish oil which is flash chromatographed over silica gel using 4:1 hexane-ethyl acetate as eluent to provide the desired product (9 g, 32%) as a yellow oil.

EXAMPLE 11

Preparation of 3-Trifluoroacetyl-3-cyanopropionaldehyde

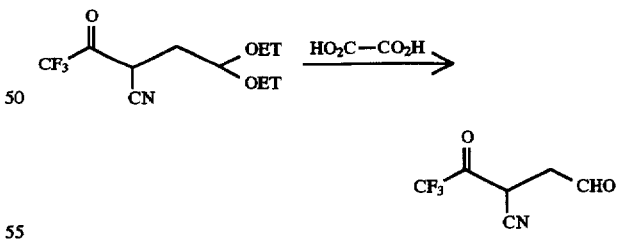

A mixture of the 2-trifluoroacetylcyanopropionaldehyde-4,4-diethyl acetal (5.0 g, 0.02 mol) and oxalic acid dihydrate (1.2 g, 0.01 mol) in 75 mL of water is heated to reflux for 20 minutes. After the reaction is allowed to cool, sodium bicarbonate (1.7 g, 0.02 mol) is added followed by 100 mL of ethyl acetate. The layers are separated and the organic phase is washed once with brine (15 mL) before being dried over magnesium sulfate. Rotary evaporation yields a dark oil which is used immediately in the next step of the reaction sequence.

EXAMPLE 12

Preparation of 2-(Trifluoromethyl)pyrrole-3-carbonitrile

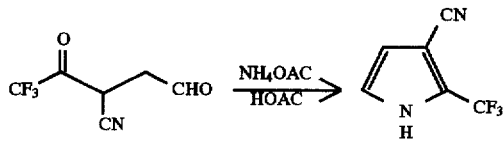

The crude aldehyde (isolated from the previous step (4.5 g) is dissolved in 50 mL of glacial acetic acid, followed by ammonium acetate (1.5 g, 0.02 mol). The mixture is heated to 65°–70° C. for one hour, allowed to cool, and is then poured into 100 mL of water. Extraction with ethyl acetate (2×75 mL) is followed by bicarbonate washing of the combined organic phases until no acid remains. The red solution is then dried over magnesium sulfate and rotary evaporated to a dark oil. Purification over silica gel using 4:1 hexane-ethyl acetate as eluent affords the 2-trifluoromethyl-3-cyanopyrrole (0.7 g, 4.3 mmol, 22% from the acetal) as a light yellow solid, mp 122°–124° C.

EXAMPLE 13

Preparation of 4,5-Dibromo-2-(trifluoromethyl)pyrrole-3-carbonitrile

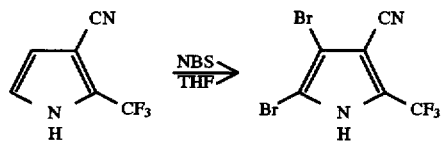

To a solution of 2-(trifluoromethyl)pyrrole-3-carbonitrile (1.0 g, 6.2 mmol) in 40 mL of tetrahydrofuran is added N-bromosuccinimide (2.2 g, 13 mmol) portionwise. The reaction mixture is allowed to stir overnight at room temperature before being quenched with saturated aqueous sodium thiosulfate (5 mL). Water (15 mL) and diethyl ether (50 mL) are added and the layers separated. The organic layer is washed with brine (10 mL) and dried over magnesium sulfate. Rotary evaporation yields a crude solid which is flash chromatographed using 2:1 hexane-ethyl acetate doped with acetic acid (2 mL per 300 mL of solvent) as eluent. The desired 2-trifluoromethyl-3-cyano-4,5-dibromopyrrole (0.8 g, 2.5 mmol, 40%) is isolated as a pale yellow solid.

EXAMPLE 14

Preparation of 4,5-Dibromo-5-methyl-2-(trifluoromethyl) pyrrole-3-carbonitrile

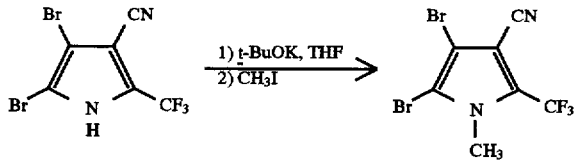

To a solution of the 2-trifluoromethyl-3-cyano-4,5-dibromopyrrole (0.5 g, 1.6 mmol) in 30 mL of dry tetrahydrofuran is added potassium tert-butoxide (0.2 g, 1.9 mmol) portionwise. The rose colored solution is allowed to stir for 20 minutes before the addition of methyl iodide (0.6 g, 4.2 mmol) neat. The resulting suspension is stirred for 5 hours before being quenched by the addition of 10 mL of water. Diethyl ether (50 mL) is also added and the layers are separated. The organic phase is washed with brine (10 mL) and dried over magnesium sulfate. Rotary evaporation yields a crude solid which is flash chromatographed over silica gel using 4:1 hexane-ethyl acetate as eluent to provide the N-methylated pyrrole (0.4 g, 1.2 mmol, 77%) as a light yellow solid, mp 123°–125° C.

EXAMPLE 15

Preparation of 3,4-Dibromo-5-nitropyrrole-2-carbonitrile

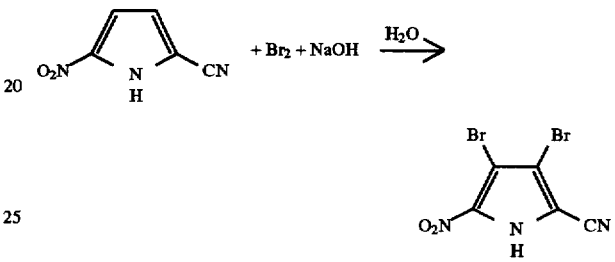

A sample of 5-nitropyrrole-2-carbonitrile (0.4 g, 0.003) is readily soluble in 10 mL of dilute sodium hydroxide (0.4 g, 0.01 mol). Bromine (0.96 g, 0.006 mol) is added dropwise which results in the deposition of a solid precipitate. Additional 10% sodium hydroxide is added until all the solid is dissolved. The solution is then stirred 15 minutes before acidifying with dilute hydrochloric acid. The white precipitate is collected and dried. The product (0.5 g, 56%) has mp 181°–186° C.

EXAMPLE 16

Preparation of 3,5-Dibromo-4-nitropyrrole-2-carbonitrile

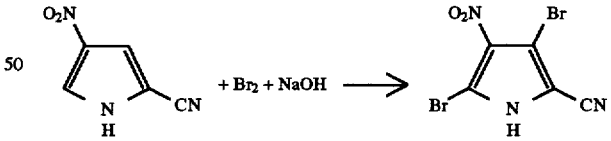

4-Nitropyrrole-2-carbonitrile (0.6 g, 0.0042 mol) is readily soluble in 15 mL of water containing sodium hydroxide (0.5 g, 0.012 mol). Bromine (1.34 g, 0.008 mol) is added dropwise, resulting in the formation of a solid precipitate. Sodium hydroxide (10% solution) is then added until the solid is dissolved. The resulting solution is stirred for 15 minutes before acidifying the solution with dilute hydrochloric acid. The white precipitate (1.0 g, 83%) has mp 170°–175° C. Calcd. for $C_5HBr_2N_3O_2$: C, 20.35; H, 0.33; N, 14.24; Br, 54.20. Found: C, 20.72; H, 0.23; N, 14.16; Br, 53.50.

EXAMPLE 17

Preparation of 2,4,5-Trichloropyrrole-3-carbonitrile

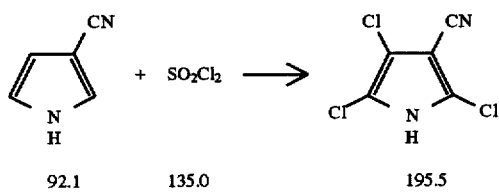

To a stirred mixture of 1.50 g (16.3 mmol) of pyrrole-3-carbonitrile in 50 mL of glacial acetic acid is added quickly dropwise 4.1 mL (51.0 mmol) of sulfuryl chloride by syringe through a rubber septum. With this addition the temperature of the reaction mixture rises from about 22° C. to 32° C. The mixture is stirred one and one-half hours and then diluted with 100 mL of water. The resulting solids are collected by filtration and washed with water. On drying, the yield is 2.23 g (70%) of white solid, mp >300° C.

EXAMPLE 18

Preparation of 2,4,5-Tribromopyrrole-3-carbonitrile

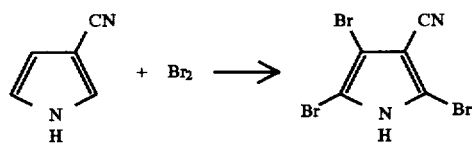

To a stirred mixture of 1.50 g (16.3 mmol) of pyrrole-3-carbonitrile in 20 mL of chloroform is added dropwise from an addition funnel a mixture of 2.5 mL (48.5 mmol) of bromine in 7.5 mL of chloroform over about 30 minutes. The temperature of the mixture rises to 38° C. and a gummy solid is formed which necessitates addition of additional chloroform (25 mL) and some warming to achieve good stirring. The mixture is stirred an additional 2 hours at room temperature and the solid product is collected by filtration and washed with chloroform. The collected solids amount to 4.55 g. Concentration of the filtrate affords another 0.58 g of product. The combined solids are slurried with boiling methylene chloride. On cooling, filtration gives 3.66 g of a pale orange powder, mp 253°–255° C.

Anal. Calcd for $C_5HBr_3N_2$: C, 18.26; H, 0.31; N, 8.52; Br, 72.91. Found: C, 18.28; H, 0.35; N, 8.52; Br, 72.74.

EXAMPLE 19

Preparation of 2,4,5-Triiodopyrrole-3-carbonitrile

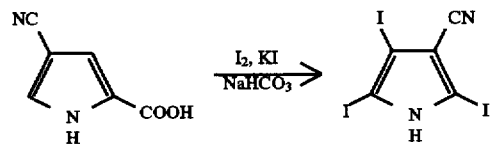

4-cyanopyrrole-2-carboxylic acid (1.36 g, 0.01 mol) is added to a warm suspension of sodium bicarbonate (16.8 g, 0.2 mol) in water (150 mL). After all the acid has dissolved, a solution of iodine (8.3 g, 0.033 mol) and potassium iodide (11.0 g, 0.066 mol) in water (50 mL) is slowly added with stirring over 1 hour. The mixture is heated at 70°–80° C. for 2 hours and cooled in an ice bath and then left in the refrigerator overnight. The solids are collected, washed well with water and are dried. Flash column chromatography on silica gel packed in methylene chloride and eluted with 3% ethyl acetate in methylene chloride gives the product as a yellow solid on crystallization from ethyl acetate (0.65 g); mp 257.0°–258.0° C.

EXAMPLE 20

Preparation of 1-Methyl-2,4,5-trichloropyrrole-3-carbonitrile

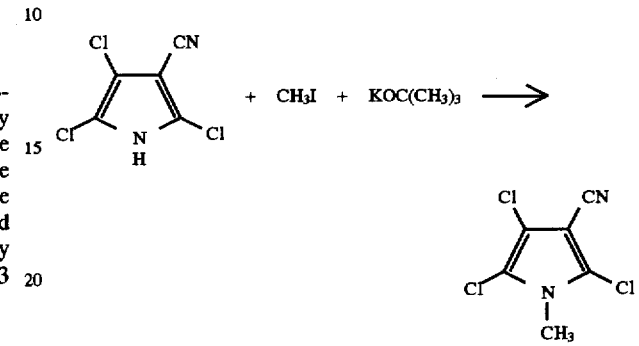

To a stirred mixture of 0.70 g (6.2 mmol) of potassium t-butoxide in 25 mL of dry THF under a nitrogen atmosphere, is added dropwise from an addition funnel 1.00 g (5.12 mmol) of 2,4,5-trichloropyrrole-3-carbonitrile in 20 mL of dry THF over a 15 minute period. After 15 minutes, 0.50 mL (8.03 mmol) of methyl iodide is added dropwise by syringe over 10 minutes. Solids are formed and after stirring for about 3 hours, the mixture is diluted with 100 mL of water. The cloudy mixture is extracted twice with ethyl acetate and the combined organic layers washed successively with dilute NaOH, water, and saturated salt solution. After drying over magnesium sulfate, the organic mixture is filtered and concentrated in vacuo to give 0.99 g of an off-white solid. Purification by chromatography on silica gel using methylene chloride affords 0.68 g of yellow-white solid which is slurried with hexane and recovered by filtration; mp 110°–114° C.

Anal. Calcd for $C_6H_3Cl_3N_2$: C, 34.40; H, 1.44; N, 13.38; Cl, 50.78. Found: C, 34.25; H, 1.50; N, 13.36; Cl, 50.88.

EXAMPLE 21

Preparation of 1-Methyl-2,4,5-tribromopyrrole-3-carbonitrile

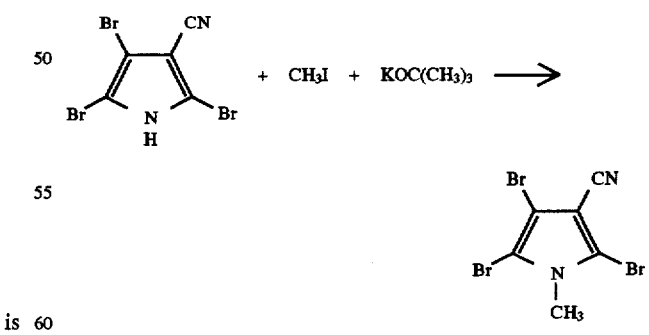

To a stirred mixture of 0.87 g (7.75 mmol) of potassium t-butoxide in 30 mL of dry THF under a nitrogen atmosphere is added dropwise from an addition funnel 2.10 g (6.39 mmol) of 2,4,5-tribromopyrrole-3-carbonitrile in 20 mL of dry THF. After 15 minutes, 0.64 mL (10.3 mmol) of methyl iodide is added by syringe over 2 minutes. After several hours at room temperature, the mixture is diluted with 100 mL of water and 75 mL of ethyl acetate. The separated water phase is extracted again with ethyl acetate and the combined organic layers are washed with dilute sodium hydroxide, water, and saturated salt solution. After drying over magnesium sulfate, the mixture is shaken with activated charcoal and filtered. Concentration in vacuo gives 1.96 g of white solid; slurrying with hexane reduces this to 1.71 g, mp 142°–152° C.

Anal. Calcd for $C_6H_3Br_3N_2$: C, 21.02; H, 0.88; N, 8.17; Br, 69.93. Found: C, 21.12; H, 0.90; N, 8.14; Br, 70.07.

EXAMPLE 22

Preparation of 1-Benzyl-2,4,5-tribromopyrrole-3-carbonitrile

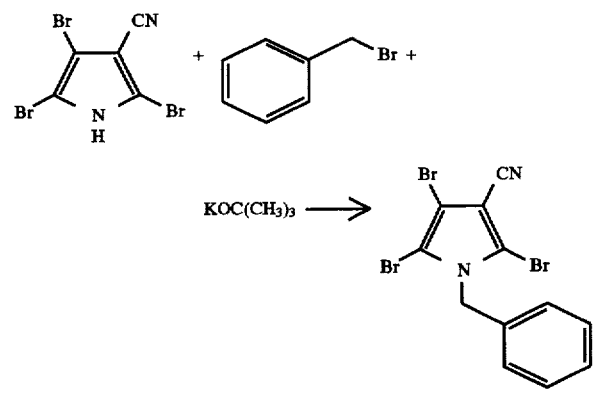

To a stirred mixture of 1.00 g (3.04 mmol) of 2,4,5-tribromopyrrole-3-carbonitrile and 0.68 g (6.1 mmol) of potassium t-butoxide in 30 mL of dry THF under a nitrogen atmosphere is added 1.10 mL of benzyl bromide. The mixture is heated to reflux and stirred overnight. After dilution with 100 mL of water and 150 mL of ethyl acetate, the organic mixture is separated and washed with salt solution, dried over magnesium sulfate, and concentrated in vacuo to leave 2.34 g of orange oil. The oil is triturated under a mixture of 5:1 hexane/ether to give a white solid collected by filtration; 0.81 g, mp 100°–103° C. The filtrate yields a second crop; 0.11 g, mp 100°–103° C.

EXAMPLE 23

Preparation of 1-Allyl-2,4,5-tribromopyrrole-3-carbonitrile

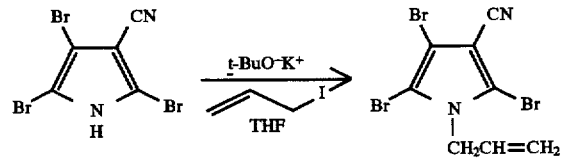

Potassium t-butoxide (0.75 g, 6.7 mmol) is added portionwise at room temperature to a solution of 2,4,5-tribromopyrrole-3-carbonitrile (2.0 g, 6.1 mmol) in anhydrous tetrafuran (20 mL). After 30 minutes allyl iodide (1.12 g, 6.7 mmol) is added dropwise and then refluxed for 2 hours. Work-up as described in Example 15 gives the product as a pale pink liquid (2.1 g).

EXAMPLE 24

Preparation of Ethyl 2,4,5-Tribromo-3-cyanopyrrole-1-acetate

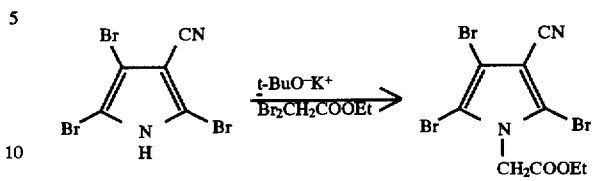

Potassium t-butoxide (0.75 g, 6.7 mmol) is added in portions at room temperature to a solution of 2,4,5-tribromopyrrole-3-carbonitrile (2.0 g, 6.1 mmol) in anhydrous tetrahydrofuran (20 mL). After 30 minutes, ethyl bromoacetate (1.12 g, 6.7 mmol) is added dropwise and the mixture stirred for 4–5 hours at room temperature. Work-up as described in Example 15 gives the product as white solid (0.42 g); mp 140°–143° C.

EXAMPLE 25

Preparation of 2,4,5-Tribromo-1-ethylpyrrole-3-carbonitrile

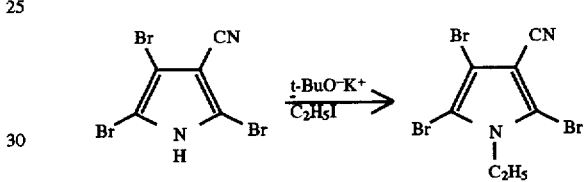

Potassium t-butoxide (0.75 g, 6.7 mmol) is added in portions at room temperature to a solution of 2,4,5-tribromopyrrole-3-carbonitrile (2.0 g, 6.1 mmol) in anhydrous tetrahydrofuran (20 mL). After 30 minutes, ethyl iodide (1.04 g, 6.7 mmol) is added dropwise. The reaction solution is stirred at room temperature for 30 minutes and then refluxed for 90 minutes. The mixture is cooled, diluted with water and extracted with ethyl acetate. The organic layer is washed with water and saturated sodium chloride and dried ($Na_2SO_4$). Evaporation of the solvent and crystallization from ether-hexanes gives a solid which is further purified by flash column chromatography on silica gel, packed with methylene chloride and eluted with 3% ethyl acetate in methylene chloride. The analytically pure sample is finally crystallized from methylene chloride-hexanes as a white solid (1.55 g); mp 108.5°–109.5° C.

EXAMPLE 26

Preparation of 2,4,5-Tribromo-1-ethylpyrrole-3-carbonitrile

In the same manner described for the preparation of 2,4,5-tribromo-1-ethylpyrrole-3-carbonitrile in Example 23, using the requisite cyanotrihalopyrrole and appropriate alkylating agent, the additional analogs illustrated below are prepared:

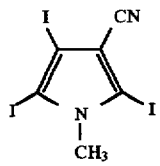

m.p. 211–214° C.

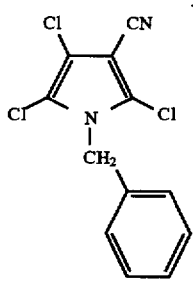
m.p. 87–91° C.

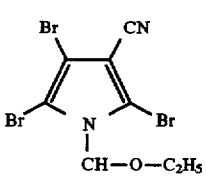
m.p. 113–117° C.

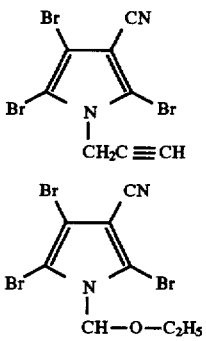
m.p. 144–147° C.

EXAMPLE 27

Preparation of 2,4,5-Tribromopyrrole-1,3-dicarbonitrile

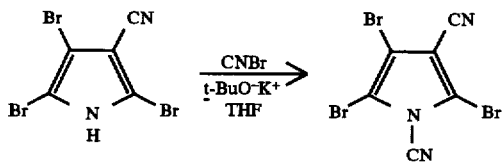

Potassium t-butoxide (614 mg, 5.74 mmol) is added in portions at room temperature to a solution of 2,4,5-tribromopyrrole-3-carbonitrile (1.50 g, 4.56 mmol) in anhydrous tetrahydrofuran (20 mL). After 15 minutes a solution of cyanogen bromide (177 mg, 5.74 mmol) in tetrahydrofuran (5 mL) is added dropwise. The reaction solution is stirred at room temperature overnight as it turns cloudy. The mixture is diluted with water and extracted with ethyl acetate. The organic layer is washed with water and saturated sodium chloride and dried over (Na₂SO₄). Evaporation of the solvent and crystallization of the residue from ether gives a white solid (1.20 g); mp 195.0°–197.5° C.

EXAMPLE 28

Preparation of 3,4,5-Tribromopyrrole-2-carbonitrile

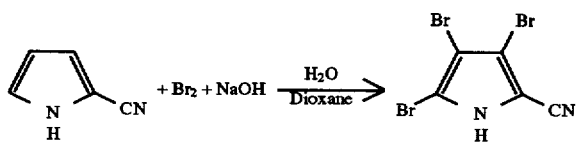

Sodium hydroxide (3.2 g, 0.08 mol) is dissolved in 100 mL of water followed by the addition of pyrrole-2-carbonitrile (2.6 g, 0.027 mol). A few mL of dioxane is added to make the mixture homogenous. Then bromine (12.96 g, 0.081 mol) is added in small portions at 28°–35° C. with periodic cooling. Before the addition is complete, solids begin to precipitate. Everything is brought back into solution by the addition of 10% sodium hydroxide. Then the remaining bromine is added and the solution stirred for 15 minutes before acidifying with dilute hydrochloric acid. The white solid (7.4 g, 84%) is collected and, after drying, has mp 215°–218° C.

Calcd for C₅HN₂Br₃: C, 18.25; H, 0.30; N, 8.51; Br, 72.92. Found: C, 18.06; H, 0.37; N, 8.39; Br, 72.72.

EXAMPLE 29

Preparation of 3,4,5-Tribromo-1-methyl-pyrrole-2-carbonitrile

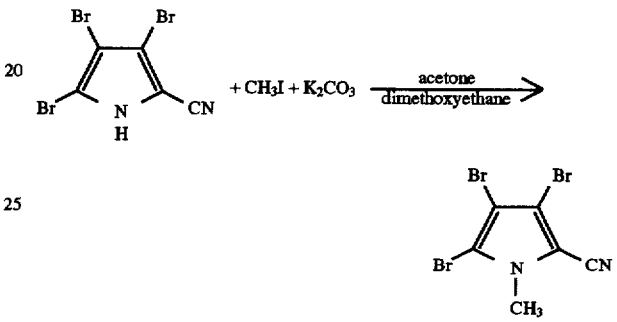

3,4,5Tribromo-pyrrole-2-carbonitrile (1.0 g, 0.003 mol) is dissolved in a mixture of acetone (20 mL) and dimethoxyethane (10 mL). Potassium carbonate (0.45 g, 0.0033 mol) is added followed by methyl iodide (0.478 g, 0.0033 mol). After stirring overnight at room temperature, the mixture is poured into water precipitating a white solid. The solid (0.8 g, 80%) has mp 115°–119° C.

Calcd for C₆H₃Br₃N₂: C, 21.00; H, 0.87; N, 8.17; Br, 69.94. Found: C, 20.98; H, 0.94; N, 8.05; Br, 69.55.

EXAMPLE 30

Preparation of 3,5-Dibromo-pyrrole-2,4-dicarbonitrile

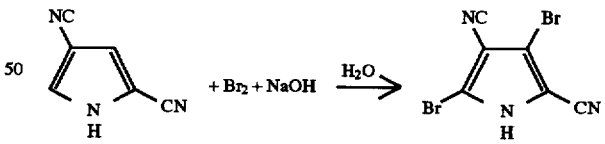

Pyrrole-2,4-dicarbonitrile (0.5 g, 0.004 mol) is readily soluble in 15 mL of water containing sodium hydroxide (0.5 g, 0.012 mol). Bromine (1.34 g, 0.008 mol) is then added and the solution stirred for 15 minutes. Thin layer chromatography (90/10 methylene chloride/acetonitrile) indicates the reaction is incomplete. Additional bromine is added and the reaction monitored by Tlc. When the reaction is complete, the mixture is acidified and a white solid collected. The solid (0.47 g, 40.8%) after recrystallization from dichloroethane (30 mL) has mp 227°–232° C. Calcd for C₆HBr₂N₃: C, 26.20; H, 0.36; N, 15.28; Br, 58.15. Found: C, 26.25; H, 0.58; N, 15.17; Br, 58.35.

EXAMPLE 31

Preparation of 3,5-Dibromo-1-methylpyrrole-2,4-dicarbonitrile

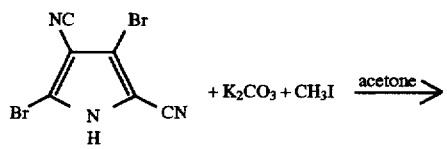

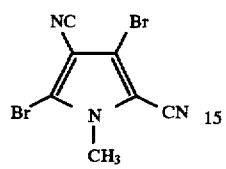

A sample (1.0 g, 0.0036 mol) of 3,5-dibromopyrrole-2,4-dicarbonitrile is readily soluble in 20 mL of acetone. Anhydrous potassium carbonate (0.64 g, 0.0046 mol) is added, and while the slurry is stirred, methyl iodide (0.68 g, 0.0047 mol) is added. The reaction can be followed by Tlc. When the reaction is complete, the mixture is poured into water precipitating a white solid. The product (0.77 g, 74%) has mp 175°–178° C.

Calcd for $C_7H_3Br_2N_3$: C, 29.08; H, 1.04; N, 14.54; Br, 55.33. Found: C, 29.09; H, 1.42; N, 14.48; Br, 54.95.

EXAMPLE 32

Preparation of 3-Bromo-2,5-dichloro-4-nitropyrrole

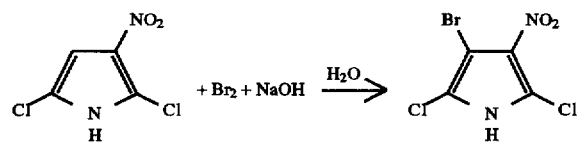

The title compound can be prepared by dissolving a sample of 2,5-dichloro-3-nitropyrrole (0.54 g, 0.003 mol) in 10 mL of dilute sodium hydroxide (0.25, 0.006), and adding bromine (0.48 g, 0.003 mol). If solid precipitates before all the bromine is added, additional base can be added. When the addition is complete, the solution can be acidified with dilute hydrochloric acid to precipitate the desired product.

EXAMPLE 33

Preparation of 4-(trifluoromethyl)pyrrole-3-carbonitrile

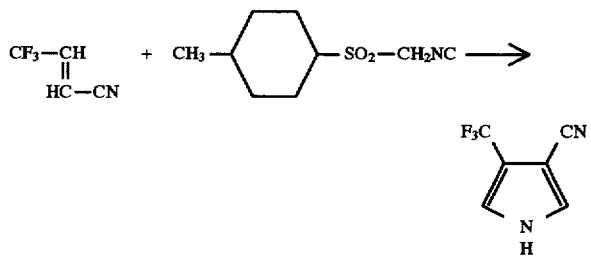

A mixture of p-tolylsulfonylmethylisocyanide (0.72 g, 3.2 mmol) and sodium hydride (0.09 g, 3.8 mmol) in anhydrous ethyl ether is treated dropwise with a solution of 4,4,4-trifluorocrotonitrile (0.38 g, 3.2 mmol) in ether and dimethyl sulfoxide over a 35 minute period, stirred at room temperature for 20 minutes and quenched with water. The phases are separated and the aqueous phase is extracted with ether. The organic phases are combined, washed with brine, dried over $MgSO_4$ and concentrated in vacuo to afford an orange solid residue. The residue is flash chromatographed using silica gel and 100:100:1 petroleum ether:ethyl ether:acetic acid followed by 100% methylene chloride to give the title product as a white solid, mp 96° to 97° C.

EXAMPLE 34

Preparation of 2,5-dibromo-4-(trifluoromethyl)pyrrole-3-carbonitrile

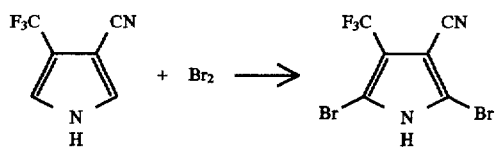

A mixture of 4-(trifluoromethyl)pyrrole-3-carbonitrile (0.10 g, 0.63 mmol) and sodium acetate (0.2 g, 2.4 mmol) in acetic acid is treated dropwise with a solution of bromine (0.23 g, 1.4 mmol) in acetic acid, stirred for 6 hours at 25° C. and poured into an aqueous metabisulfite solution. The resultant mixture is filtered and the filter cake is washed with water and air-dried to yield the title compound as a white solid, 0.11 g (58%), mp 198° to 200° C.

EXAMPLE 35

Preparation of 2,5-dibromo-1-methyl-4-(trifluoromethyl)pyrrole-3-carbonitrile

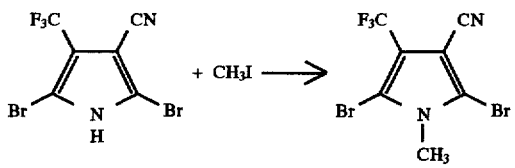

A solution of 2,5-dibromo-4-(trifluoromethyl)pyrrole-3-carbonitrile (0.10 g, 0.30 mmol) in tetrahydrofuran is treated with solid potassium t-butoxide (0.053 g, 0.49 mmol), stirred for 1 hour at 25° C., treated dropwise with methyl iodide (0.067 g, 0.47 mmol), stirred for 2 hours at 25° C. and for 1 hour at 50° C. and diluted with water and ether. The phases are separated and the organic phase is washed sequentially with water and brine, dried over $MgSo_4$ and concentrated in vacuo to afford the title compound as a white solid, 0.09 g, mp 101° to 104° C.

EXAMPLE 36

Preparation of 4,5-dibromo-1-methylpyrrole-2-carbonitrile

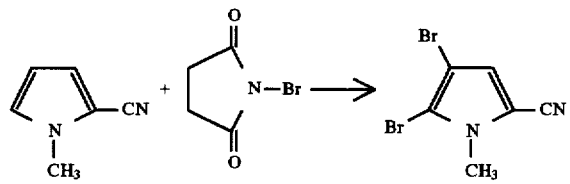

A solution of 1-methylpyrrole-2-carbonitrile (1.06 g, 0.01 mol) in tetrahydrofuran is treated with N-bromosuccinimide (5.34 g, 0.03 mol) at 25° to 30° C., stirred for 18 hours at 25° C. and concentrated in vacuo to give a residue. The residue

EXAMPLE 37

Preparation of ethyl 4-(trifluoromethyl)pyrrole-3-carboxylate

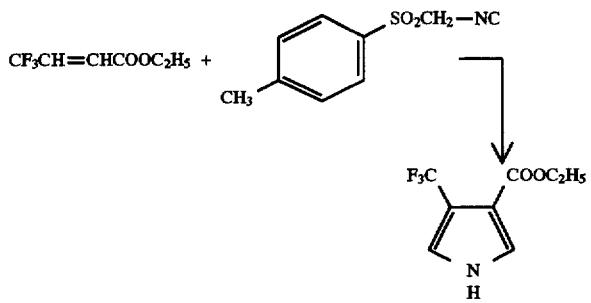

A solution of potassium t-butoxide (8.11 g, 0.075 mol) in tetrahydrofuran at –60° C. is treated dropwise with a mixture of ethyl 4,4,4-trifluorocrotonate (10.5 g, 0.063 mol) and p-tolylsulfonylmethylisocyanide (12.2 g, 0.063 mol) in tetrahydrofuran over a 1 hour period, stirred at –60° C. for 30 minutes, allowed to warm to room temperature and quenched with water. The reaction mixture is extracted with ether and ethyl acetate. The combined extracts are washed with brine, dried (MgSO$_4$) and concentrated in vacuo to give a solid residue. Recrystallization from 1,2-dichloroethane affords the title compound as a tan solid, 7.3 g (56%), mp 163° to 164° C.

EXAMPLE 38

Preparation of ethyl 1-methyl-4-(trifluoromethyl)-pyrrole-3-carboxylate

A solution of potassium t-butoxide (4.5 g, 0.04 mol) in tetrahydrofuran is treated dropwise with a solution of ethyl 4-(trifluoromethyl)pyrrole-3-carboxylate (8.3 g, 0.04 mol) in tetrahydrofuran over a 20 minute period at 20°–25° C., stirred for 30 minutes, treated dropwise with methyl iodide (5.7 g, 0.04 mol), stirred at room temperature for 24 hours and poured into water. The resultant mixture is extracted with ether and the combined extracts are washed with brine, dried (MgSO$_4$) and concentrated in vacuo to afford a brown oil residue. The residue is distilled using a Kugelrohr distillation apparatus to give a gummy solid at 80° to 85° C./0.2 mm Hg. The solid is purified using ether and basic alumina to yield the title compound as a clear oil, 6.37 g (72%), identified by NMR and elemental analyses.

is taken up in carbon tetrachloride, filtered and the filtrate is concentrated in vacuo to give a solid residue. Recrystallization from ethanol/water yields the title product as a grey solid, mp 104° to 105° C.

EXAMPLE 39

Preparation of 1-methyl-4-(trifluoromethyl)pyrrole-3-carboxylic acid

A mixture of ethyl 1-methyl-4-(trifluoromethyl)pyrrole-3-carboxylate (4.4 g, 0.02 mol) and 4N sodium hydroxide (5 ml, 0.02 mol) in ethanol is stirred for 24 hours at room temperature, diluted with water and extracted with ether. The aqueous phase is acidified with 10% HCl and filtered. The filter cake is washed with water and dried in vacuo at 45° C. to afford the title compound as an off-white solid, 2.4 g (62%), mp 210° to 212° C.

EXAMPLE 40

Preparation of 1-methyl-4-(trifluoromethyl)pyrrole-3-carbonitrile

A mixture of 1-methyl-4-(trifluoromethyl)pyrrole-3-carboxylic acid (1.93 g, 0.01 mol) in acetonitrile at 40°–45° C. is treated dropwise with chlorosulfonylisocyanate (1.41 g, 0.01 mol), heated at 40° C. for 24 hours, cooled to room temperature, treated with dimethylformamide (1.46 g, 0.02 mol), heated at 40° C. for 8 hours, cooled to room temperature, stirred for 48 hours at room temperature and poured into water. The resultant mixture is extracted with ethyl acetate. The extracts are combined, washed sequentially with water and brine, dried (MgSO$_4$) and concentrated in vacuo to afford an oily solid residue. The residue is taken up in ethyl acetate, washed with 1% aqueous sodium hydroxide, dried (MgSO$_4$) and concentrated in vacuo to give a yellow oil residue. Kugelrohr distillation at 100° to 110° C./2 mm Hg yields the title product as a white solid, 0.95 g (54%).

EXAMPLE 41

Preparation of phenyl 2,3,5-tribromo-4-cyanopyrrole-1-carboxylate

-continued

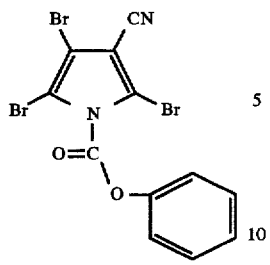

A mixture of 7.0 g of 2,4,5-tribromopyrrole-3-carbonitrile and 2.9 g of potassium t-butoxide in tetrahydrofuran is treated with 13.8 g of phenyl chloroformate, heated at reflux temperature for 12 hours, cooled, poured into water and filtered. The solid filter cake is washed with water and dried in vacuo to afford the title compound. A sample is recrystallized from a mixture of ethyl acetate and methylcyclohexane to give colorless crystals, mp 128° to 129° C.

EXAMPLE 42

Preparation of methyl 2,3,5-tribromo-4-cyanopyrrole-1-carboxylate

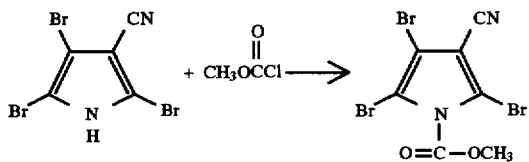

A solution of 2,4,5-tribromopyrrole-3-carbonitrile (3.0 g, 0.091 mol) in tetrahydrofuran is treated portionwise with potassium t-butoxide (1.33 g, 0.012 mol) at room temperature, stirred for 20 minutes, treated dropwise with a solution of methyl chloroformate (1.29 g, 0.014 mol) in tetrahydrofuran, stirred for 2½ days, poured into water and extracted with ether. The combined ether extracts are washed with brine, dried over MgSO$_4$ and concentrated in vacuo to give a brown solid residue. The residue is recrystallized from ethyl acetate/hexanes to afford the title compound as a tan solid, 1.4 g (39.5%) mp 119.50° to 122.0° C.

Using the above procedure and substituting the appropriate chloroformate, the following compounds are obtained:

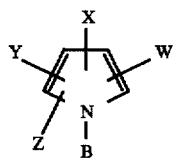

| R | mp °C. |
|---|---|
| OCH=CH$_2$ | 112–113 |
| OCH$_2$CH=CH$_2$ | 86–89 |

EXAMPLE 43

Preparation of 2,4,5-tribromo-1-(p-chlorobenzoyl)pyrrole-3-carbonitrile

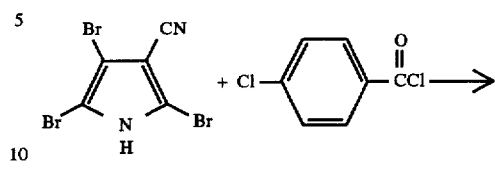

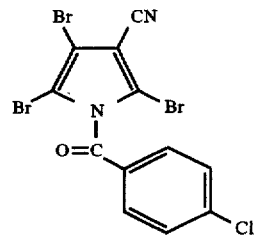

A mixture of 2,4,5-tribromopyrrole-3-carbonitrile (5.0 g, 0.015 mol) and potassium t-butoxide (2.0 g, 0.018 mol) in dry tetrahydrofuran is stirred for 10 minutes at room temperature, treated dropwise with a solution of p-chlorobenzoyl chloride (3.25 g, 0.018 mol) in tetrahydrofuran, heated at reflux temperature for 3 hours, cooled and diluted with a mixture of water and ethyl acetate. The organic phase is separated, washed with brine, dried over Na$_2$SO$_4$ and concentrated in vacuo to afford a tan solid residue. Recrystallization from benzene gives the title compound as a cream colored solid, 2.9 g (41.4%), mp 154°–157° C.

Using the above procedure and substituting p-methoxybenzoyl chloride gives 2,4,5-tribromo-1-(p-methoxybenzoyl)pyrrole-3-carbonitrile, mp 86° to 89° C.

What is claimed is:

1. A method for treating, controlling, preventing or protecting a warm-blooded animal from infestation or infection by helminths, acarids or arthropod endo- or ectoparasites which comprises administering or applying to said animal an anthelmintically, acaricidally or endo- or ectoparasiticidally effective amount of a pyrrole carbonitrile or nitropyrrole compound wherein the compound has the structure:

(I)

wherein
W is CN or NO$_2$;
X is CN, Br, Cl, I or CF$_3$;
Y is H, Br, Cl, I or CF$_3$;
Z is H, Br, Cl or I; and
B is CR, $$\overset{O}{\underset{}{\|}}$$
CR, hydrogen,
C$_1$–C$_6$ alkyl optionally substituted with one to three halogen atoms,
one tri(C$_1$–C$_4$ alkyl)silyl, one hydroxy,
one cyano,
one or two $C_1$–$C_4$ alkoxy groups optionally substituted with one to three halogen atoms,
one $C_1$–$C_4$ alkylthio,
one phenyl optionally substituted with one to three halogen atoms, one to three $C_1$–$C_4$ alkyl groups or one to three $C_1$–$C_4$ alkoxy groups,
one phenoxy group optionally substituted with one to three halogen atoms, one to three $C_1$–$C_4$ alkyl groups or one to three $C_1$–$C_4$ alkoxy groups,
one benzyloxy group optionally substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group optionally substituted with one to three halogen atoms,
one $C_2$–$C_6$ alkenylcarbonyloxy group optionally substituted with one to three halogen atoms,
one phenylcarbonyloxy group optionally substituted with one to three halogen atoms, one to three $C_1$–$C_4$ alkyl groups or one to three $C_1$–$C_4$ alkoxy groups,
one phenylcarbonyl group optionally substituted with one to three halogen atoms, one to three $C_1$–$C_4$ alkyl groups or one to three $C_1$–$C_4$ alkoxy groups,
one $C_1$–$C_6$ alkoxycarbonyl group optionally substituted with one to three halogen atoms or one to three $C_1$–$C_4$ alkoxy groups, or
one benzyloxycarbonyl group optionally substituted on the phenyl ring with one to three halogen atoms, one to three $C_1$–$C_4$ alkyl groups or one to three $C_1$–$C_4$ alkoxy groups,
one $C_1$–$C_6$ alkyloxycarbonyloxy group optionally substituted with one to three halogen atoms,
$C_3$–$C_6$ alkenyl optionally substituted with one to three halogen atoms or one phenol group,
$C_3$–$C_6$ alkynyl optionally substituted with one to three halogen atoms or one phenyl group,
$C_1$–$C_6$ alkyl substituted with one to three halogen atoms and one $C_1$–$C_4$ alkoxy group,
$C_3$–$C_6$ 1,2-alkadienyl, or cyano;

R is
$C_1$–$C_6$ alkyl optionally substituted with one to three halogen atoms,
one hydroxy,
one cyano,
one or two $C_1$–$C_4$ alkoxy groups optionally substituted with one to three halogen atoms,
one $C_1$–$C_4$ alkylthio,
one phenyl optionally substituted with one to three halogen atoms, one to three $C_1$–$C_4$ alkyl groups or one to three $C_1$–$C_4$ alkoxy groups,
one phenoxy group optionally substituted with one to three halogen atoms, one to three $C_1$–$C_4$ alkyl groups or one to three $C_1$–$C_4$ alkoxy groups,
one benzyloxy group optionally substituted on the phenyl ring with one to three halogen atoms, one to three $C_1$–$C_4$ alkyl groups or one to three $C_1$–$C_4$ alkoxy groups,
one $C_1$–$C_6$ alkylcarbonyloxy group optionally substituted with one to three halogen atoms,
one $C_2$–$C_6$ alkenylcarbonyloxy group optionally substituted with one to three halogen atoms,
one phenylcarbonyloxy group optionally substituted with one to three halogen atoms, one to three $C_1$–$C_4$ alkyl groups or one to three $C_1$–$C_4$ alkoxy groups,
one $C_1$–$C_6$ alkoxycarbonyl group optionally substituted with one to three halogen atoms or one to three $C_1$–$C_4$ alkoxy groups, or
one benzyloxycarbonyl group optionally substituted on the phenyl ring with one to three halogen atoms, one to three $C_1$–$C_4$ alkyl groups or one to three $C_1$–$C_4$ alkoxy groups,
$C_3$–$C_6$ alkenyl optionally substituted with one to three halogen atoms or one phenyl group,
$C_3$–$C_6$ alkynyl optionally substituted with one to three halogen atoms or one phenyl group,
phenyl optionally substituted with one to three halogen atoms, one or two $C_1$–$C_4$ alkyl groups, one or two $C_1$–$C_4$ alkoxy groups, $CF_3$, CN, $NO_2$, di($C_1$–$C_4$alkyl)amino or $C_1$–$C_4$ alkanoylamino,
phenoxy optionally substituted with one to three halogen atoms, one or two $C_1$–$C_4$ alkyl groups, one or two $C_1$–$C_4$ alkoxy groups, $CF_3$, CN or $NO_2$, di($C_1$–$C_4$alkyl)amino or $C_1$–$C_4$ alkanoylamino,
$C_1$–$C_6$ alkoxy optionally substituted with one to three halogen atoms,
$C_2$–$C_6$ alkenyloxy optionally substituted with one to three halogen atoms,
di($C_1$–$C_4$alkyl)amino,
N-($C_1$–$C_4$alkyl)-N-phenylamino or N-($C_1$–$C_4$ alkyl)-N-halophenylamino, or
$C_3$–$C_6$ polymethyleneimino.

2. The method according to claim 1, for controlling the infestation and infection which comprises orally administering thereto an agronomically acceptable carrier containing about 0.5 ppm to 1000 ppm of the compound.

3. The method according to claim 1, for controlling the infestation and infection which comprises parenterally administering thereto an agronomically acceptable carrier containing about 0.01 mg/kg to 100 mg/kg of animal body weight per day of the compound.

4. The method according to claim 1, for preventing and treating the infestation and infection which comprises orally administering thereto a prophylatically effective amount of the compound.

5. The method according to claim 1, wherein the animal is selected from the group consisting of cattle, sheep, horses, swine, goats, poultry, fish, deer and other domestic and wild animals.

6. The method according to claim 1, for controlling, treating and preventing the infestation and infection of cattle, sheep, horses, swine, goats, dogs and cats which comprises topically applying a composition containing the pyrrole carbonitrile or nitropyrrole compound to the skin, hide and hair of said animal.

7. The method according to claim 6, wherein the composition is applied in solid or liquid form.

8. The method according to claim 7, wherein the composition is applied as an aqueous dip or spray containing about 0.5 ppm to 5000 ppm of the compound.

9. The method according to claim 1, wherein the helminths are flukes and wherein the compound has the structure:

(T)

wherein
X is CN, Br, Cl, I or $CF_3$;
Y is H, Br, Cl, I or $CF_3$;

Z is H, Br, Cl or I; and

B is

hydrogen, $C_1$–$C_6$ alkyl optionally substituted with one to three halogen atoms, one or two $C_1$–$C_4$ alkoxy groups optionally substituted with one to three halogen atoms, one phenyl optionally substituted with one to three halogen atoms, one to three $C_1$–$C_4$ alkyl groups or one to three $C_1$–$C_4$ alkoxy groups, one $C_1$–$C_6$ alkylcarbonyloxy group optionally substituted with one to three halogen atoms, one phenylcarbonyl group optionally substituted with one to three halogen atoms, one to three $C_1$–$C_4$ alkyl groups or one to three $C_1$–$C_4$ alkoxy groups, or one $C_1$–$C6$ alkyloxycarbonyloxy group optionally substituted with one to three halogen atoms, or $C_1$–$C_6$alkyl substituted with one to three halogen atoms and one $C_1$–$C_4$ alkoxy group;

R is phenyl optionally substituted with one to three halogen atoms, one or two $C_1$–$C_4$ alkyl groups, one or two $C_1$–$C_4$ alkoxy groups, $CF_3$, CN, $NO_2$, di($C_1$–$C_4$alkyl)amino or $C_1$–$C_4$ alkanoylamino, $C_1$–$C_6$ alkoxy optionally substituted with one to three halogen atoms, or $C_2$–$C_6$ alkenyloxy optionally substituted with one to three halogen atoms.

10. The method according to claim 9, wherein the compounds is selected from the group consisting of 2,4,5-tribromo-1-(hydroxymethyl)pyrrole-3-carbonitrile pivalate (ester), 2,4,5-tribromo-1-methylpyrrole-3-carbonitrile, 2,4,5-tribromo-1-(methoxymethyl)pyrrole-3-carbonitrile, 2,4,5-tribromo-1-(isopropoxymethyl)pyrrole-3-carbonitrile, 2,4,5-tribromo-1-(p-chlorobenzoyl)pyrrole-3-carbonitrile, allyl 2,3,5-tribromo-4-cyanopyrrole-1-carboxylate, 2,4,5-tribromopyrrole-3-carbonitrile, 2,4,5-tribromo-1-(ethoxymethyl)pyrrole-3-carbonitrile, 2,4,5-tribromo-1-ethylpyrrole-3-carbonitrile, 2,4,5-tribromo-1-(2-chloro-1-ethoxyethyl)pyrrole-3-carbonitrile, 2,4,5-tribromo-1-(hydroxymethyl)pyrrole-3-carbonitrile, acetate (ester), ethyl 1-(2,3,5-tribromo-4-cyanopyrrol-1-yl)ethyl carbonate, 2,4,5-tribromo-1-(p-chlorobenzyl)pyrrole-3-carbonitrile, methyl 2,3,5-tribromo-4-cyanopyrrole-1-carboxylate, vinyl 2,3,5-tribromo-4-cyanopyrrole-1-carboxylate, 2,4,5-tribromo-1-(p-methoxybenzoyl)pyrrole-3-carbonitrile, 2,5-Dibromo-1-(2-chloro-1-ethoxyethyl)-4-(trifluoromethyl)pyrrole-3-carbonitrile, 2,5-Dibromo-1-methylpyrrole-3,4-dicarbonitrile, and 2,4,5-tribromo-1-(chloromethyl)pyrrole-3-carbonitrile.

11. The method according to claim 1, wherein the helminths are nematodes and wherein the compound has the structure:

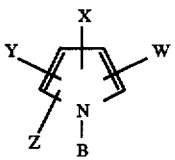

wherein

W is CN or $NO_2$;

X is CN, Br, Cl, I or $CF_3$;

Y is Br, Cl, I or $CF_3$;

Z is H, Br, Cl or I; and

B is hydrogen, $C_1$–$C_6$ alkyl optionally substituted with one to three halogen atoms, one or two $C_1$–$C_4$ alkoxy groups optionally substituted with one to three halogen atoms, one phenyl optionally substituted with one to three halogen atoms, one to three $C_1$–$C_4$ alkyl groups or one to three $C_1$–$C_4$ alkoxy groups, one phenylcarbonyloxy group optionally substituted with one to three halogen atoms, one to three $C_1$–$C_4$ alkyl groups or one to three $C_1$–$C_4$ alkoxy groups, or one $C_1$–$C_6$ alkyloxycarbonyloxy group optionally substituted with one to three halogen atoms, $C_3$–$C_6$ alkenyl optionally substituted with one to three halogen atoms or one phenyl group, $C_3$–$C_6$ alkynyl optionally substituted with one to three halogen atoms or one phenyl group, or cyano.

12. The method according to claim 11, wherein the compound is selected from the group consisting of 2,4,5-trichloro-1-methylpyrrole-3-carbonitrile, 2,4,5-tribromo-1-methylpyrrole-3-carbonitrile, 2,4,5-tribromopyrrole-1,3-dicarbonitrile, 4,5-dibromo-1-methylpyrrole-2-carbonitrile, 3,4,5-tribromopyrrole-2-carbonitrile, 2-chloro-4-nitropyrrole, 2,5-dichloro-3-nitropyrrole, 2,3-dichloro-4-nitropyrrole, 2,3,5-trichloro-4-nitropyrrole, 2,5-dibromo-3-nitropyrrole, 2,3-dibromo-4-nitropyrrole, 2,4,5-trichloropyrrole-3-carbonitrile, 4,5-dichloropyrrole-3-carbonitrile, 2,4,5-tribromopyrrole-3-carbonitrile, 4,5-dibromopyrrole-2-carbonitrile, 3,4,5-tribromo-1-methylpyrrole-2-carbonitrile, 2,5-diiodo-1-methylpyrrole-3-carbonitrile, 5-nitropyrrole-5-carbonitrile, 4-nitropyrrole-2-carbonitrile, 3,4-dibromo-5-nitropyrrole-2-carbonitrile, 3,5-dibromo-4-nitropyrrole-2-carbonitrile, 1-(ethoxymethyl)-5-nitropyrrole-2-carbonitrile, allyl-2,4,5-tribromopyrrole-3-carbonitrile, and 4,5-dibromo-1-(ethoxymethyl)-2-(trifluoromethyl)pyrrole-3-carbonitrile.

13. The method according to claim 1, wherein the ectoparasites are Acarina and wherein the compound has the structure:

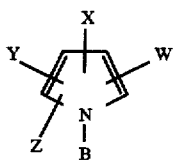

(I)

wherein
W is CN or NO$_2$;
X is CN, Br, Cl, I or CF$_3$;
Y is H, Br, Cl, I or CF$_3$;
Z is H, Br, Cl or I; and
B is

$$\overset{O}{\underset{CR,}{\|}}$$

hydrogen,
  C$_1$–C$_6$ alkyl optionally substituted with one to three halogen atoms,
    one or two C$_1$–C$_4$ alkoxy groups optionally substituted with one to three halogen atoms,
    one phenyl optionally substituted with one to three halogen atoms, one to three C$_1$–C$_4$ alkyl groups or one to three C$_1$–C$_4$ alkoxy groups,
    one C$_1$–C$_6$ alkylcarbonyloxy group optionally substituted with one to three halogen atoms,
    one C$_1$–C$_6$ alkoxycarbonyl group optionally substituted with one to three halogen atoms or one to three C$_1$–C$_4$ alkoxy groups, or
    one C$_1$–C$_6$ alkyloxycarbonyloxy group optionally substituted with one to three halogen atoms,
  C$_3$–C$_6$ alkenyl optionally substituted with one to three halogen atoms or one phenyl group,
  C$_3$–C$_6$ alkynyl optionally substituted with one to three halogen atoms or one phenyl group, or
  C$_1$–C$_6$ alkyl substituted with one to three halogen atoms and one C$_1$–C$_4$ alkoxy group;
R is phenoxy optionally substituted with one to three halogen atoms, one or two C$_1$–C$_4$ alkyl groups, one or two C$_1$–C$_4$ alkoxy groups, CF$_3$, CN or NO$_2$, di(C$_1$–C$_4$alkyl)amino or C$_1$–C$_4$ alkanoylamino,
  C$_1$–C$_6$ alkoxy optionally substituted with one to three halogen atoms, or
  C$_2$–C$_6$ alkenyloxy optionally substituted with one to three halogen atoms.

14. The method according to claim 13, wherein the compound is selected from the group consisting of
4,5-dibromopyrrole-2-carbonitrile,
3,4,5-tribromo-1-methylpyrrole-2-carbonitrile,
2,5-diiodo-1-methylpyrrole-3-carbonitrile,
2,4,5-tribromo-1-(ethoxymethyl)pyrrole-3-carbonitrile,
3,4,5-tribromopyrrole-2-carbonitrile,
4-nitropyrrole-2-carbonitrile,
1-methyl-5-nitropyrrole-2-carbonitrile,
3,4,5-tribromo-1-(2-propynyl)pyrrole-2-carbonitrile,
4,5-dibromo-1-methylpyrrole-3-carbonitrile,
4,5-dibromo-1-(ethoxymethyl)-2-(trifluoromethyl)pyrrole-3-carbonitrile,
2,4,5-tribromo-1-(hydroxymethyl)pyrrole-3-carbonitrile, pivalate (ester),
2,4,5-tribromo-1-(3,4-dichlorobenzyl)pyrrole-3-carbonitrile,
2,4,5-tribromo-1-(isopropoxymethyl)pyrrole-3-carbonitrile,
2,4,5-tribromo-1-(2-chloro-1-ethoxyethyl)pyrrole-3-carbonitrile,
2,4,5-tribromo-1-(hydroxymethyl)pyrrole-3-carbonitrile, acetate (ester),
ethyl 1-(2,3,5-tribromo-4-cyanopyrrol-1-yl)ethyl carbonate,
phenyl 2,3,5-tribromo-4-cyanopyrrole-1-carboxylate,
2,4,5-tribromo-1-(methoxymethyl)pyrrole-3-carbonitrile,
2,4,5-tribromopyrrole-3-carbonitrile,
2,4,5-tribromo-1-methylpyrrole-3-carbonitrile,
4,5-dibromopyrrole-2-carbonitrile, and
allyl 2,3,5-tribromo-4-cyanopyrrole-1-carboxylate.

15. The method according to claim 1, wherein the ectoparasites are fleas and wherein the compound has the structure:

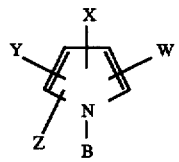

(I)

wherein
W is CN or NO$_2$;
X is CN, Br or Cl;
Y is H Br or Cl;
Z is H, Br or Cl; and
B is hydrogen,
  C$_1$–C$_6$ alkyl optionally substituted with one to three halogen atoms,
    one or two C$_1$–C$_4$ alkoxy groups optionally substituted with one to three halogen atoms, or
    one C$_1$–C$_6$ alkyloxycarbonyloxy group optionally substituted with one to three halogen atoms,
  C$_3$–C$_6$ alkenyl optionally substituted with one to three halogen atoms or one phenyl group,
  C$_3$–C$_6$ alkynyl optionally substituted with one to three halogen atoms or one phenyl group,
  C$_3$–C$_6$ 1,2-alkadienyl, or cyano.

16. The method according to claim 15, wherein the compound is selected from the group consisting of
2,4,5-tribromo-1-(methoxymethyl)pyrrole-3-carbonitrile,
2,4,5-tribromo-1-methylpyrrole-3-carbonitrile,
4,5-dibromo-1-methylpyrrole-2-carbonitrile,
3,4,5-tribromo-1-methylpyrrole-2-carbonitrile,
3,4,5-tribromo-1-(2-propynyl)pyrrole-2-carbonitrile,
3,4,5-tribromopyrrole-2-carbonitrile,
4,5-dibromopyrrole-2-carbonitrile,
2,3,5-trichloro-1-methylpyrrole-3-carbonitrile,
2,4,5-tribromo-1-(2-propynyl)pyrrole-3-carbonitrile,
3,4,5-tribromo-1-(1,2-propadienyl)pyrrole-2-carbonitrile, and
2-bromo-1-methyl-4-nitropyrrole.

* * * * *